United States Patent
Chouaib et al.

(10) Patent No.: US 11,137,404 B2
(45) Date of Patent: Oct. 5, 2021

(54) METHOD FOR ASSESSING THE RESPONSE TO PD-1/PDL-1 TARGETING DRUGS

(71) Applicant: INSTITUT GUSTAVE ROUSSY, Villejuif (FR)

(72) Inventors: Salem Chouaib, Villejuif (FR); Yosra Messai, Villejuif (FR); Muhammad Zaeem Noman, Thionville (FR)

(73) Assignee: INSTITUT GUSTAVE ROUSSY, Villejuif (FR)

( * ) Notice: Subject to any disclaimer, the term of this patent is extended or adjusted under 35 U.S.C. 154(b) by 496 days.

(21) Appl. No.: 16/061,667

(22) PCT Filed: Dec. 16, 2016

(86) PCT No.: PCT/EP2016/081485
§ 371 (c)(1),
(2) Date: Jun. 13, 2018

(87) PCT Pub. No.: WO2017/103147
PCT Pub. Date: Jun. 22, 2017

(65) Prior Publication Data
US 2018/0364241 A1   Dec. 20, 2018

(30) Foreign Application Priority Data
Dec. 18, 2015 (EP) .................................... 15307050

(51) Int. Cl.
*G01N 33/574* (2006.01)
*A61K 39/395* (2006.01)

(52) U.S. Cl.
CPC ............... *G01N 33/57438* (2013.01); *G01N 33/57484* (2013.01); *G01N 2800/52* (2013.01)

(58) Field of Classification Search
CPC .... G01N 33/57484; A61P 35/04; A61P 35/00; C12Q 1/6886; C12Q 2600/158; C12Q 2600/156
See application file for complete search history.

(56) References Cited

FOREIGN PATENT DOCUMENTS

WO   WO 2013/173223   11/2013

OTHER PUBLICATIONS

Crouzet et al, Journal of Clinical Oncology, 33: suppl1 Abstract 11053, May 2015.*
Frew et al, Ann Rev Pathol Mech Dis, 10:263-289, published online Oct. 2014.*
Gnarra et al, Nat Genet 7:85-90, 1994.*
Motzer et al, J Clinical Oncology, 33:1430-1437, 2014.*
Kammerer-Jacquet, Int J Cancer, 140:142-148, 2017.*
Debernardo et al, J Clin Oncol, 33: suppl1 Abstract 5595, May 2015.*
Noman, M. Z. et al. "PD-L1 is a novel direct target of HIF-1α, and its blockade under hypoxia enhanced MDSC-mediated T cell activation" *The Journal of Experimental Medicine*, Apr. 28, 2014, pp. 781-790, vol. 211, No. 5.
Kaelin, W. G., Jr. "Molecular Basis of the VHL Hereditary Cancer Syndrome" *Nature Reviews*, Sep. 2002, pp. 673-682, vol. 2.
Beuselinck, B. et al. "Molecular Subtypes of Clear Cell Renal Cell Carcinoma Are Associated with Sunitinib Response in the Metastatic Setting" *Clinical Cancer Research*, Mar. 15, 2015, pp. 1329-1339, vol. 21, No. 6.
Kammerer-Jacquet, S.-F. et al. "Independent association of PD-L1 expression with noninactivated VHL clear cell renal cell carcinoma—A finding with therapeutic potential" *International Journal of Cancer*, 2017, pp. 142-148, vol. 140, No. 1.
Messai, Y. et al. "HIF-2α/ITPR1 axis: A new saboteur of NK-mediated lysis" *OncoImmunology*, Feb. 2015, pp. e985951-1-e985951-3, vol. 4, No. 2.
Messai, Y. et al. "ITPR1 Protects Renal Cancer Cells against Natural Killer Cells by Inducing Autophagy" *Cancer Research*, Dec. 1, 2014, pp. 6820-6832, vol. 74, No. 23.
Messai, Y. et al. "Renal Cell Carcinoma Programmed Death-ligand 1, a New Direct Target of Hypoxia-inducible Factor-2 Alpha, is Regulated by von Hippel-Lindau Gene Mutation Status" *European Urology*, 2016, pp. 623-632, vol. 70, No. 4.
Noman, M. Z. et al. "Crosstalk between CTC, Immune System and Hypoxic Tumor Microenvironment" *Cancer Microenvironment*, 2014, pp. 153-160, vol. 7, No. 3.
Sutphin, P. D. et al. "Targeting the Loss of the von Hippel-Lindau Tumor Suppressor Gene in Renal Cell Carcinoma Cells" *Cancer Research*, Jun. 15, 2007, pp. 5896-5905, vol. 67, No. 12.
Tykodi, S. S. "Pd-1 as an emerging therapeutic target in renal cell carcinoma: current evidence" *OncoTargets and Therapy*, Jul. 25, 2014, pp. 1349-1359, vol. 7.
Vaziri, S. A. J. et al. "Differing von Hippel Lindau genotype in paired primary and metastatic tumors in patients with clear cell renal cell carcinoma" *Frontiers in Oncology*, May 28, 2012, pp. 1-19, vol. 2, No. 51.
Zitvogel, L. et al. "Targeting PD-1/PD-L1 interactions for cancer immunotherapy" *OncoImmunology*, Nov. 2012, pp. 1223-1225, vol. 1, No. 8.
Written Opinion in International Application No. PCT/EP2016/081485, dated Mar. 9, 2017, pp. 1-7.

* cited by examiner

*Primary Examiner* — Mark Halvorson
(74) *Attorney, Agent, or Firm* — Saliwanchik, Lloyd & Eisenschenk

(57) ABSTRACT

The present invention relates to a method for assessing the response of a patient to a treatment with anti-PD-1/PDL-1 drugs based on the status of the VHL gene (von Hippel-Lindau).

10 Claims, 8 Drawing Sheets
Specification includes a Sequence Listing.

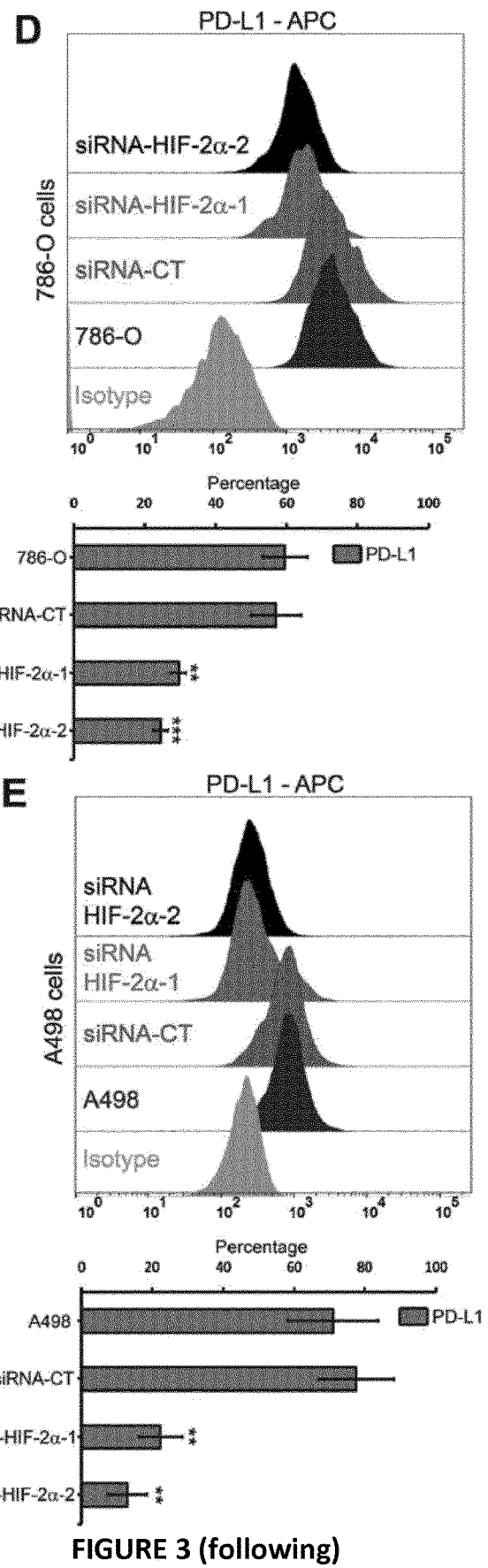
FIGURE 3 (following)

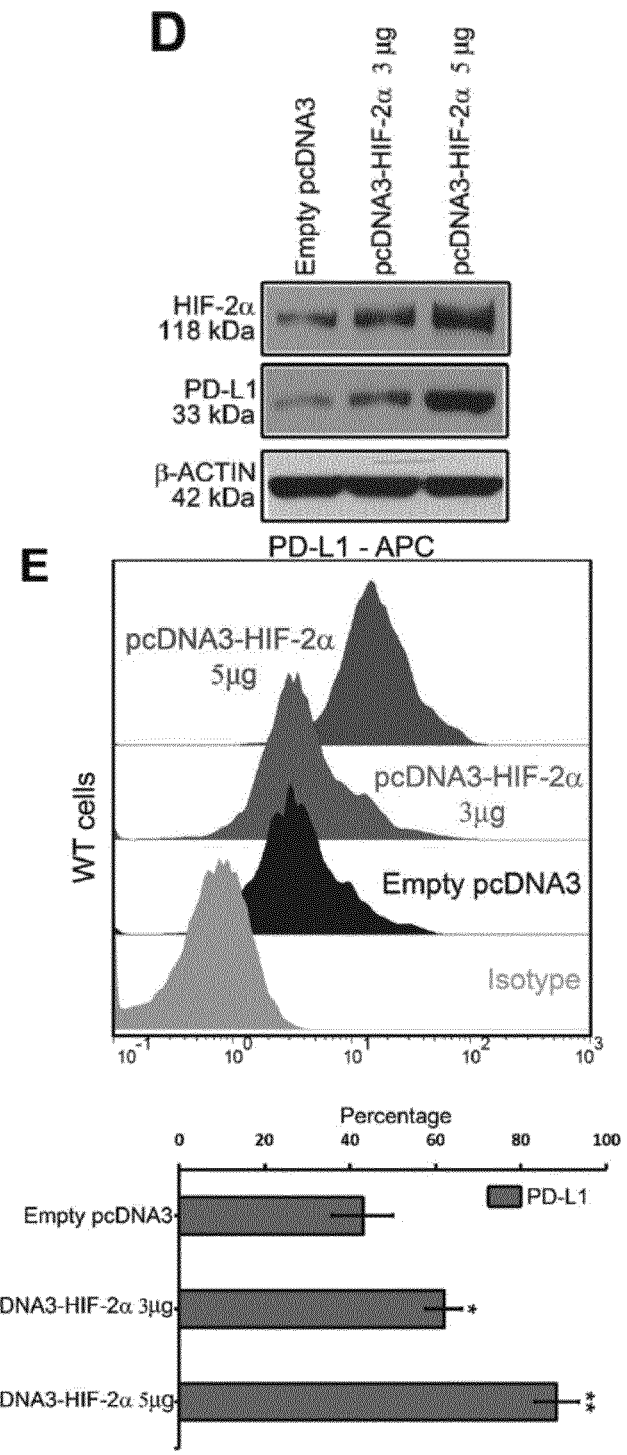
FIGURE 4 (following)

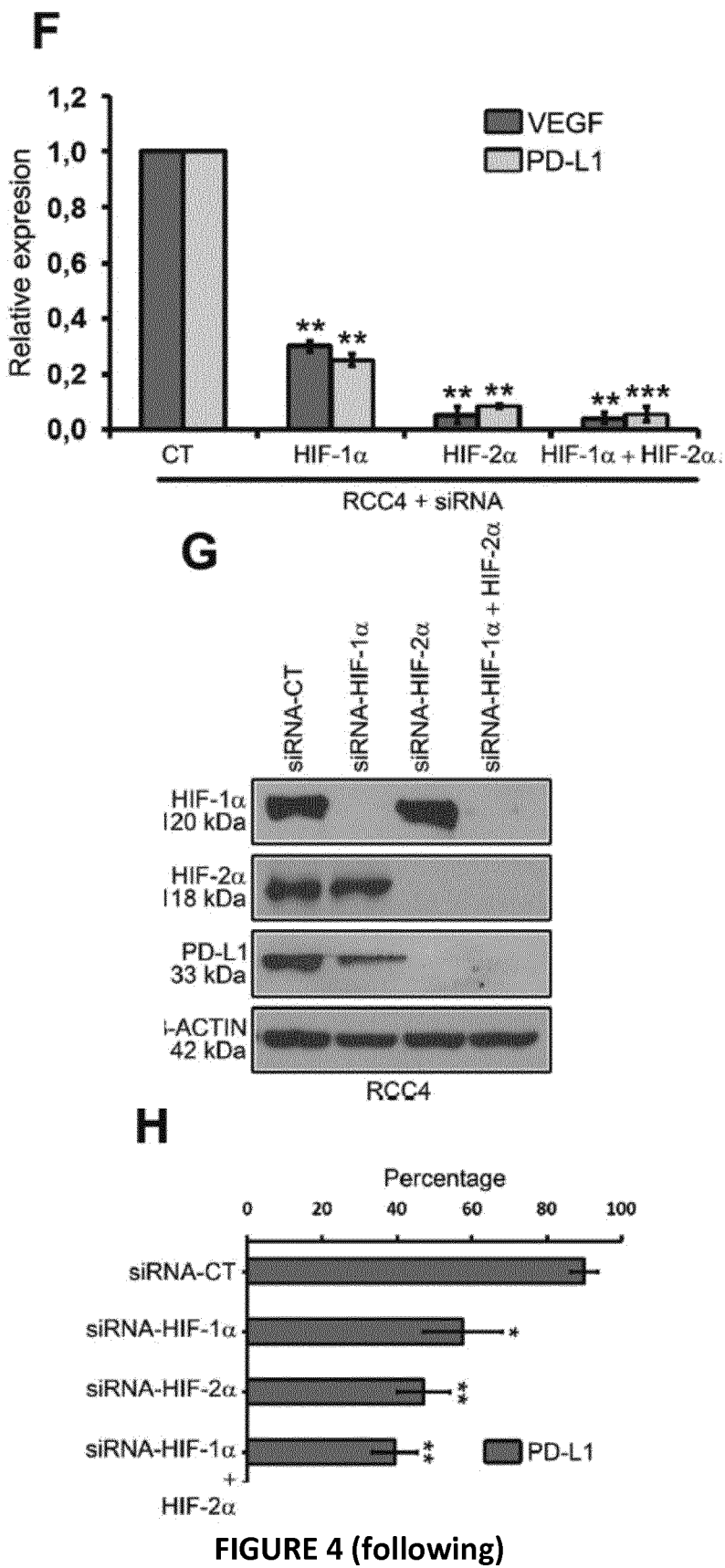
FIGURE 4 (following)

SEQUENCE LISTING

<160> NUMBER OF SEQ ID NOS: 20

<210> SEQ ID NO 1
<211> LENGTH: 18
<212> TYPE: DNA
<213> ORGANISM: artificial sequence
<220> FEATURE:
<223> OTHER INFORMATION: primer

<400> SEQUENCE: 1
tcagttccct ggcaacat                                                 18

<210> SEQ ID NO 2
<211> LENGTH: 20
<212> TYPE: DNA
<213> ORGANISM: artificial sequence
<220> FEATURE:
<223> OTHER INFORMATION: primer

<400> SEQUENCE: 2
accaagtttg tggagctgag                                               20

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
ggaggagacg taatccagca                                               20

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
attctcctcc tctgctttcg                                               20

```
<210> SEQ ID NO 5
<211> LENGTH: 24
<212> TYPE: DNA
<213> ORGANISM: artificial sequence
<220> FEATURE:
<223> OTHER INFORMATION: primer

<400> SEQUENCE: 5
tcctcatggg ttatgtgtag tttg                                              24

<210> SEQ ID NO 6
<211> LENGTH: 20
<212> TYPE: DNA
<213> ORGANISM: artificial sequence
<220> FEATURE:
<223> OTHER INFORMATION: primer

<400> SEQUENCE: 6
tccctcttag tgcctctcca                                                   20

<210> SEQ ID NO 7
<211> LENGTH: 21
<212> TYPE: DNA
<213> ORGANISM: artificial sequence
<220> FEATURE:
<223> OTHER INFORMATION: primer

<400> SEQUENCE: 7
tgcactgagt ctgtttcctc a                                                 21

<210> SEQ ID NO 8
<211> LENGTH: 21
<212> TYPE: DNA
<213> ORGANISM: artificial sequence
<220> FEATURE:
<223> OTHER INFORMATION: primer

<400> SEQUENCE: 8
ccatctttga ctacccaggt g                                                 21

<210> SEQ ID NO 9
<211> LENGTH: 20
<212> TYPE: DNA
<213> ORGANISM: artificial sequence
<220> FEATURE:
<223> OTHER INFORMATION: primer

<400> SEQUENCE: 9
gatttcaccg aaggtcagga                                                   20

<210> SEQ ID NO 10
<211> LENGTH: 18
<212> TYPE: DNA
<213> ORGANISM: artificial sequence
<220> FEATURE:
<223> OTHER INFORMATION: primer

<400> SEQUENCE: 10
ctacctgcag gcggacag                                                     18

<210> SEQ ID NO 11
<211> LENGTH: 20
<212> TYPE: DNA
<213> ORGANISM: artificial sequence
<220> FEATURE:
```

<223> OTHER INFORMATION: primer

<400> SEQUENCE: 11
cggacaggat tgacagattg                                               20

<210> SEQ ID NO 12
<211> LENGTH: 20
<212> TYPE: DNA
<213> ORGANISM: artificial sequence
<220> FEATURE:
<223> OTHER INFORMATION: primer

<400> SEQUENCE: 12
caaatcgctc caccaactaa                                               20

<210> SEQ ID NO 13
<211> LENGTH: 20
<212> TYPE: DNA
<213> ORGANISM: artificial sequence
<220> FEATURE:
<223> OTHER INFORMATION: primer

<400> SEQUENCE: 13
gcgctagact ccgagaacat                                               20

<210> SEQ ID NO 14
<211> LENGTH: 23
<212> TYPE: DNA
<213> ORGANISM: artificial sequence
<220> FEATURE:
<223> OTHER INFORMATION: primer

<400> SEQUENCE: 14
tggccactta ctacctgacc ctt                                           23

<210> SEQ ID NO 15
<211> LENGTH: 17
<212> TYPE: DNA
<213> ORGANISM: artificial sequence
<220> FEATURE:
<223> OTHER INFORMATION: primer

<400> SEQUENCE: 15
gcacccatgg cagaagg                                                  17

<210> SEQ ID NO 16
<211> LENGTH: 21
<212> TYPE: DNA
<213> ORGANISM: artificial sequence
<220> FEATURE:
<223> OTHER INFORMATION: primer

<400> SEQUENCE: 16
ctcgattgga tggcagtagc t                                             21

<210> SEQ ID NO 17
<211> LENGTH: 20
<212> TYPE: DNA
<213> ORGANISM: artificial sequence
<220> FEATURE:
<223> OTHER INFORMATION: primer

<400> SEQUENCE: 17
ctgaagacag gatggagaag                                               20

```
<210> SEQ ID NO 18
<211> LENGTH: 18
<212> TYPE: DNA
<213> ORGANISM: artificial sequence
<220> FEATURE:
<223> OTHER INFORMATION: primer

<400> SEQUENCE: 18
gcagagtgcg gcagaatg                                                    18

<210> SEQ ID NO 19
<211> LENGTH: 19
<212> TYPE: DNA
<213> ORGANISM: artificial sequence
<220> FEATURE:
<223> OTHER INFORMATION: primer

<400> SEQUENCE: 19
tgtaccgctg catgatcag                                                   19

<210> SEQ ID NO 20
<211> LENGTH: 22
<212> TYPE: DNA
<213> ORGANISM: artificial sequence
<220> FEATURE:
<223> OTHER INFORMATION: primer

<400> SEQUENCE: 20
agttcatgtt cagaggtgac tg                                               22
```

METHOD FOR ASSESSING THE RESPONSE TO PD-1/PDL-1 TARGETING DRUGS

CROSS-REFERENCE TO RELATED APPLICATION

This application is the U.S. national stage application of International Patent Application No. PCT/EP2016/081485, filed Dec. 16, 2016.

The Sequence Listing for this application is labeled "Seq-List.txt" which was created on Apr. 26, 2018 and is 4 KB. The entire content of the sequence listing is incorporated herein by reference in its entirety.

FIELD OF THE INVENTION

The present invention relates to the fields of genetics, immunology and medicine. The present invention more specifically relates to an in vitro or ex vivo method of assessing the sensitivity of a subject having a cancer to treatment by a PD-1/PD-L1 targeting agent.

BACKGROUND OF THE INVENTION

Tumor cells act on host immunity in several ways to evade immune defenses in the tumor microenvironment. This phenomenon is generally called "cancer immune escape." One of the most important components in this system is an immunosuppressive co-signal (immune checkpoint) mediated by the PD-1 receptor and its ligand, PD-L1. PD-1 is mainly expressed on activated T cells, whereas PD-L1 is expressed on several types of tumor cells. Preclinical studies have shown that inhibition of the interaction between PD-1 and PD-L1 enhances the T-cell response and mediates antitumor activity. Several clinical trials of PD-1/PD-L1 signal-blockade agents have exhibited dramatic antitumor efficacy in patients with certain types of solid or hematological malignancies.

However, the accumulated data from clinical trials for solid tumors revealed that the antitumor response rate of PD-1 inhibitors seems not so high. In addition, PD-1 inhibitors are very expensive and not devoid of adverse reactions. Therefore, it is necessary to identify predictive biomarkers that allow selection of appropriate patients for improving therapeutic efficacy.

SUMMARY OF THE INVENTION

The invention provides, in a first aspect, an in vitro or ex vivo method for selecting a patient affected with a tumor for a treatment with a PD-1/PD-L1 targeting agent or for determining whether a patient affected with a tumor is susceptible to benefit from a treatment with a PD-1/PD-L1 targeting agent, wherein the method comprises:

(a) detecting if cells from a sample from said patient present or not a loss of function of the von Hippel-Lindau (VHL) gene, wherein the loss of function of the VHL gene is predictive of the responsiveness of said patient to a treatment with a PD-1/PD-L1 targeting agent, and (b) selecting patients with loss of function of the VHL gene as suitable for a treatment with a PD-1/PD-L1 targeting agent.

Preferably, the method further comprises a step of providing a sample from said patient.

Preferably, the sample is a cancer sample.

Preferably, the method further comprises a step of administering a PD-1/PD-L1 targeting agent to said patient with loss of function of the VHL gene.

In a second aspect, the invention also provides a PD-1/PD-L1 targeting agent for use in the treatment of a cancer in a patient wherein the patient presents a loss of function of the VHL gene.

Preferably, the cancer is a renal cancer, more preferably a clear cell renal cell carcinoma (ccRCC).

The loss of function of the VHL gene can be detected by measuring the activity of the VHL protein.

The loss of function of the VHL gene can also be detected by measuring the molecular weight of the VHL protein.

The loss of function of the VHL gene can also be detected by measuring the expression level of the VHL gene.

The loss of function of the VHL gene can also be determined by detecting the presence or the absence of mutations in VHL genes, preferably germline mutations, somatic mutations, nonsense mutations, missense mutations, promoter repression such as promoter hypermethylation and any combination thereof.

The loss of function of the VHL gene can yet be detected by one method described above or any combination of at least two of the methods described above.

Preferably, the PD-1/PD-L1 targeting agent is a molecule targeting PD-L1, a molecule targeting PD-1 or a molecule targeting the PD-1/PD-L1 complex, more preferably the PD-1/PD-L1 targeting agent is a PD-1 or a PD-1/PD-L1 antagonist.

Alternatively, the PD-1/PD-L1 targeting agent is an antibody targeting PD-1, PD-L1 or the PD-1/PD-L1 complex.

The PD-1/PD-L1 agent is preferably selected from the group consisting of Nivolumab (Opdivo, Bristol-Myers Squibb), Pembrolizumab (Keytruda, MK-3475, Merck), Pidilizumab (CT-011, Cure Tech), AMP-224 (Amplimmune/GlaxoSmith Klien), AMP-514 (Amplimmune/GlaxoSmith Klien), BMS 936559 (Bristol Myers Squibb), MPDL3280A (Atezolizumab, Roche), Durvalumab (MPDLI4736, MedImmune/AstraZeneca), Avelumab (MSB0010718C, Merck Serono/Pfizer) and a combination thereof.

The patient is preferably a mammal, more preferably a human, and even more preferably an adult human.

Preferably, the patient has already received at least one line of treatment.

Preferably, the patient suffers from a metastatic cancer and/or a cancer at an advanced stage.

In a third aspect, the invention also provides, a kit for selecting a patient affected with a tumor for a treatment with a PD-1/PD-L1 targeting agent, wherein the kit comprises means for the detection of the loss of function of the VHL gene, preferably selected from the group consisting of a pair of primers targeting the VHL gene, primers targeting the VHL mRNA, a pair of primers targeting the VHL cDNA, a probe targeting the VHL cDNA, a probe targeting the VHL mRNA, a probe targeting the VHL DNA, a VHL substrate, an antibody specific of the VHL protein, and a combination thereof. By VHL gene is intended the wildtype gene or a mutated gene. The probe, primer, substrate or antibody can be specific to a wildtype VHL or a mutated VHL. The kit may comprise a combination of a detection means specific for wildtype and mutated VHL.

In a forth aspect, the invention also provides, the use of the loss of function of the VHL gene as a biomarker for selecting a patient affected with a tumor for a treatment with a PD-1/PD-L1 targeting agent.

In a fifth aspect, the invention also provides the use of a kit for selecting a patient affected with a tumor for a treatment with a PD-1/PD-L1 targeting agent, wherein the kit comprises means for the detection of the loss of function of the VHL gene, preferably selected from the group consisting of a pair of primers targeting the VHL gene, primers targeting the VHL mRNA, a pair of primers targeting the VHL cDNA, a probe targeting the VHL cDNA, a probe targeting the VHL mRNA, a probe targeting the VHL DNA, a VHL substrate, an antibody specific of the VHL protein, and a combination thereof.

DETAILED DESCRIPTION OF THE INVENTION

The inventors have discovered that tumor from ccRCC patients with VHL biallelic inactivation (i.e. loss of function) display a significant increase in PD-L1 expression as compared with ccRCC tumors carrying one VHL wild-type allele, paving a new avenue for the selection of patients that are susceptible to benefit from a treatment with PD-1/PD-L1 targeting agent.

Definitions

The term "cancer" or "tumor", as used herein, refers to the presence of cells possessing characteristics typical of cancer-causing cells, such as uncontrolled proliferation, and/or immortality, and/or metastatic potential, and/or rapid growth and/or proliferation rate, and/or certain characteristic morphological features. This term refers to any type of malignancy (primary or metastases) in any type of subject. In particular, the term encompasses renal cancer at any stage of progression.

As used herein, the term "marker" and "biomarker" are interchangeable and refer to biological parameters that aid the selection of patients who will benefit from a specific treatment. This term refers particularly to "tumor biomarkers". It is a measurable indicator for predicting the responsiveness of a patient to a specific treatment, in particular a treatment with a PD-1/PD-L1 targeting agent. A biomarker can be found in the blood, urine, stool, tumor tissue, or other tissues or bodily fluids of some patients with cancer, in particular in a tumor tissue.

As used herein, the term "cancer sample" refers to any sample containing tumoral cells derived from the patient. In particular, tumoral cells may be obtained from fluid sample such as blood, plasma, urine and seminal fluid samples as well as from biopsies, organs, tissues or cell samples. In a preferred embodiment, tumoral cells are obtained from tumor biopsy or resection sample from the patient. Preferably, the sample contains only tumoral cells. Optionally, samples containing tumoral cells may be treated prior to their use. As example, a tumor cell enrichment sorting may be performed.

As used herein, the term "treatment", "treat" or "treating" refers to any act intended to ameliorate the health status of patients such as therapy, prevention, prophylaxis and retardation of the disease.

As used herein, the term "effective amount" refers to a quantity of a pharmaceutical composition which prevents, removes or reduces the deleterious effects of the renal cancer.

As used herein, the term "loss of function" or "loss of function of a gene" are interchangeable and refer to a situation in which a cell presents a reduced or abolished function of the protein coded by said gene. In particular, the loss of function can be due to mutations of the gene or to other mechanisms leading to a reduce expression of the gene.

As used herein, the term "allele" refers to one of alternative forms of the same gene or same genetic locus. Different alleles can result in protein with different functions. Diploid organisms, such as humans, have two sets of chromosomes, referred to as homologous chromosomes. On each chromosome, they have one copy of each gene and, therefore, one allele. If both alleles are the same, they are homozygous with respect to that gene. If the alleles are different, they are heterozygous with respect to that gene.

The term "probe", as used herein, means a strand of DNA or RNA of variable length (about 20-1000 bases long) which can be labelled. The probe is used in DNA or RNA samples to detect the presence of nucleotide sequences (the DNA or RNA target) that are complementary to the sequence in the probe.

The term "primer", as used herein, means a strand of short DNA sequence that serves as a starting point for DNA synthesis. The polymerase starts polymerization at the 3'-end of the primer, creating a complementary sequence to the opposite strand. "PCR primers" are chemically synthesized oligonucleotides, with a length between 10 and 30 bases, preferably about 20 bases long.

The terms "quantity," "amount," and "level" are used interchangeably herein and may refer to an absolute quantification of a molecule in a sample, or to a relative quantification of a molecule in a sample, i.e., relative to another value such as relative to a reference value as taught herein, or to a range of values for the biomarker. These values or ranges can be obtained from a single patient or from a group of patients.

In a first aspect, the invention relates to an in vitro or ex vivo method for selecting a patient affected with a tumor for a treatment with a PD-1/PD-L1 targeting agent or for determining whether a patient affected with a tumor is susceptible to benefit from a treatment with a PD-1/PD-L1 targeting agent, wherein the method comprises:

(a) detecting if cells from a sample from said patient present or not a loss of function of the von Hippel-Lindau (VHL) gene, wherein the loss of function of the VHL gene is predictive of the responsiveness of said patient to a treatment with a PD-1/PD-L1 targeting agent, and (b) selecting patients with loss of function of the VHL gene as suitable for a treatment with a PD-1/PD-L1 targeting agent.

In a second aspect, the present invention also concerns a PD-1/PD-L1 targeting agent for use in the treatment of a cancer in a patient wherein the patient presents a loss of function of the VHL gene.

Patient

As used herein, the terms "subject", "individual" or "patient" are interchangeable and refer to an animal, preferably to a mammal, even more preferably to a human. However, the term "patient" can also refer to non-human animals, in particular mammals such as dogs, cats, horses, cows, pigs, sheep and non-human primates, among others, that are in need of a treatment.

In a preferred embodiment of the above mentioned method and PD-1/PD-L1 targeting agent for use, the subject is a human, preferably an adult human. In particular, the human is a human of at least 50 years old, preferably a human of at least 60 years old.

In a particular embodiment of the above mentioned method and PD-1/PD-L1 targeting agent for use, the subject has a family history of cancer, preferably of clear cell renal cell carcinoma (ccRCC) or other risk factors. In this case, the subject can be a human of at least 40 years old.

In another particular embodiment of the above mentioned method and PD-1/PD-L1 targeting agent for use, the subject has relapse from a previous cancer, preferably a renal cancer, more preferably a ccRCC cancer.

In another particular embodiment of the above mentioned method and PD-1/PD-L1 targeting agent for use, the patient has already received at least one line of cancer treatment, preferably a renal cancer treatment, more preferably a ccRCC cancer treatment.

In another particular embodiment of the above mentioned method and PD-1/PD-L1 targeting agent for use, the patient suffers from a metastatic cancer and/or a cancer at an advanced stage, preferably a renal cancer, more preferably a ccRCC cancer.

Cancer

The method above mentioned and the PD-1/PD-L1 targeting agent for use can be used to guide treatment for any appropriate cancer. In various embodiments, the cancer comprises an acute lymphoblastic leukemia; acute myeloid leukemia; adrenocortical carcinoma; AIDS-related cancer; AIDS-related lymphoma; anal cancer; appendix cancer; astrocytomas; atypical teratoid/rhabdoid tumor; basal cell carcinoma; bladder cancer; brain stem glioma; brain tumor, brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma; breast cancer; bronchial tumors; Burkitt lymphoma; cancer of unknown primary site (CUP); carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrom macroglobulinemia; or Wilm's tumor. The cancer can include without limitation an acute myeloid leukemia (AML), breast carcinoma, cholangiocarcinoma, colorectal adenocarcinoma, extrahepatic bile duct adenocarcinoma, female genital tract malignancy, gastric adenocarcinoma, gastroesophageal adenocarcinoma, gastrointestinal stromal tumor (GIST), glioblastoma, head and neck squamous carcinoma, leukemia, liver hepatocellular carcinoma, low grade glioma, lung bronchioloalveolar carcinoma (BAC), non-small cell lung cancer (NSCLC), lung small cell cancer (SCLC), lymphoma, male genital tract malignancy, malignant solitary fibrous tumor of the pleura (MSFT), melanoma, multiple myeloma, neuroendocrine tumor, nodal diffuse large B-cell lymphoma, non-epithelial ovarian cancer (non-EOC), ovarian surface epithelial carcinoma, pancreatic adenocarcinoma, pituitary carcinomas, oligodendroglioma, prostatic adenocarcinoma, retroperitoneal or peritoneal carcinoma, retroperitoneal or peritoneal sarcoma, small intestinal malignancy, soft tissue tumor, thymic carcinoma, thyroid carcinoma, or uveal melanoma.

In some embodiments, the cancer comprises a breast cancer, triple negative breast cancer, metaplastic breast cancer (MpBC), head and neck squamous cell carcinoma (HNSCC), human papilloma virus (HPV)-positive HNSCC, HPV-negative/TP53-mutated HNSCC, metastatic HNSCC, oropharyngeal HNSCC, non-oropharyngeal HNSCC, a carcinoma, a sarcoma, a melanoma, a luminal A breast cancer, a luminal B breast cancer, HER2+ breast cancer, a high microsatellite instability (MSI-H) colorectal cancer, a microsatellite stable colorectal cancer (MSS), non-small cell lung cancer (NSCLC), chordoma, or adrenal cortical carcinoma. The carcinoma can be a carcinoma of the breast, colon, lung, pancreas, prostate, Merkel cell, ovary, liver, endometrial, bladder, kidney or cancer of unknown primary (CUP). The sarcoma can be a liposarcoma, chondrosarcoma, extraskeletal myxoid chondrosarcoma or uterine sarcoma. In some embodiments, the sarcoma comprises an alveolar soft part sarcoma (ASPS), angiosarcoma, breast angiosarcoma, chondrosarcoma, chordoma, clear cell sarcoma, desmoplastic small round cell tumor (DSRCT), epithelioid hemangioendothelioma (EHE), epithelioid sarcoma, endometrial stromal sarcoma (ESS), ewing sarcoma, fibromatosis, fibrosarcoma, giant cell tumour, leiomyosarcoma (LMS), uterine LMS, liposarcoma, malignant fibrous histiocytoma (MFH/UPS), malignant peripheral nerve sheath tumor (MPNST), osteosarcoma, perivascular epithelioid cell tumor (PEComa), rhabdomyosarcoma, solitary fibrous tumor (SFT), synovial sarcoma, fibromyxoid sarcoma, fibrous hamartoma of infancy, hereditary leiomyomatosis, angiomyolipoma, angiomyxoma, atypical spindle cell lesion (with fibrohistiocytic differentiation), chondroblastoma, dendritic cell sarcoma, granular cell tumor, high grade myxoid sarcoma, high-grade myoepithelial carcinoma, hyalinizing fibroblastic sarcoma, inflammatory myofibroblastic sarcoma, interdigitating dendritic cell tumor, intimal sarcoma, leiomyoma, lymphangitic sarcomatosis, malignant glomus tumor, malignant myoepithelioma, melanocytic neoplasm, mesenchymal neoplasm, mesenteric glomangioma, metastatic histocytoid neoplasm, myoepithelioma, myxoid sarcoma, myxoid stromal, neurilemmoma, phyllodes, rhabdoid, round cell, sarcoma not otherwise specified (NOS), sarcomatous mesothelioma, schwannoma, spindle and round cell sarcoma, spindle cell or spinocellular mesenchymal tumor.

In one embodiment, the cancer can be selected in the group consisting of melanoma, lung cancer, ovarian cancer, head and neck cancer, bladder cancer, gastric cancer, renal cancer, colon cancer; esophageal cancer, hepatocellular cancer, breast cancer, hematopoietic cancer such as lymphoma or leukemia.

In a preferred embodiment, the cancer is selected from the group consisting of renal cancer, lung cancer, especially non-small-cell lung cancer, melanoma, lymphoma, mesothelioma, colon cancer, pancreatic cancer, breast cancer, melanoma, and glioblastoma.

Optionally, the cancer may be selected from the group consisting of non-small-cell lung cancer, melanoma, and renal-cell cancer.

In a preferred embodiment, the cancer is a renal cell carcinoma, and more specifically a clear cell renal cell carcinoma (ccRCC), in particular a sporadic ccRCC.

Sample

The above mentioned method relates to the detection of a loss of function of the VHL gene in a sample from said patient. The sample can be a non-cancerous sample or a cancer sample.

A non-cancerous sample can be used to detect the loss of function of the VHL gene, in particular when there is a familial history of cancer, preferably a ccRCC cancer, thereby supporting the hypothesis of inherited mutations. Inherited mutations can be detected in any cell of a patient.

Preferably, the sample used to detect the loss of function of the VHL gene is a cancer sample, even more preferably a ccRCC cancer sample.

A cancer sample may contain a mix of cancer cells and normal cells. When it is the case, a tumor cell enrichment sorting may be performed. Preferably, the cancer sample is a sample containing only cancer cells or at least 70%, preferably 80%, 90%, 95% of cancer cells.

In a preferred embodiment, the above mentioned method is performed on cancer cells from a cancer sample from said patient.

The above mentioned method can also necessitate the use of a normal sample, as a way of comparison to the sample, preferably to the cancer sample. Preferably, the normal sample is a renal cell normal sample. The normal sample can be a sample from the same patient or from another patient. The normal sample can be a sample from the same patient when there is no reason to suspect that the patient cancer result from inherited mutations. The normal sample can also be from another patient, preferably a normal or healthy patient, i.e. a patient who does not suffer from a cancer, especially from a ccRCC cancer.

The above mentioned method may also comprises a step of obtaining or providing a sample from said patient.

VHL Gene

The von Hippel-Lindau tumor suppressor also known as pVHL (also called HRCA1; RCA1; VHL1 or VHL) is encoded by the VHL gene. It is defined in databases as Uniprot P40337; OMIM 608537. Reference sequences are provided for mRNA by NM_000551 and for protein by NP_000542.

The above mentioned method and PD-1/PD-L1 targeting agent for use relate to the detection of a loss of function of the VHL gene.

The loss of function of the VHL gene can be due to the presence of two non-functional VHL alleles, in particular by mutation of both alleles, by mutation of one allele and loss of heterozygosity, by mutation of one allele and a repressed expression of the other, for instance due to a promoter silencing, for instance a hypermethylation of the promoter, or by repression of the expression of the two alleles.

Mutations in VHL gene are predictive of the responsiveness of the patient to a therapy by PD-1/PD-L1 targeting agents. Non-limiting examples of such mutations are listed below:

M1fs*20 M1I E10G E12K P25L S38F S38P G39S P40S E41V E51Q E52K M54fs A56fs*11 R58fs*9 P59fs*8 V62fs*5 V62fs*68 L63P R64P S65L S65A S65* S65W S65fs*2 V66_Q73del S68* S68P S68W E70* E70K S72P S72fs*87 Q73* V74D V74G I75del I75fs F76del F76I F76L F76S C77* C77fs N78S N78H N78fs N78I N78K N78T R79P S80N S80R S80I P81S P81fs*78 R82P R82_V84del V84L L85P P86H P86L P86S P86A P86R P86fs V87_W88del W88R W88C W88* W88S L89R L89H L89P N90I N90fs*69 N90fs D92-P97del G93C G93D G93S P95R Q96* Q96P Y98fs*61 Y98F Y98H Y98N Y98* P99fs*60 L101P L101G L101R G104fs*23 G104fs*55 T105P R107fs*52 R107P R108fs*51 R108fs I109N S111N S111G S111C S111R Y112H Y112N R113* G114R G114C G114S H115N H115Y H115Q H115R H115fs*44 L116V W117* W177R W117C L118P L118R F119L F119S L188-F119del D121G D121Y D121E A122E T124fs*35 D126G D126Y L128P L128R L128F L128fs*31 L129LE V130L N131fs*2 N131fs*28 N131fs*27 N131K N131T Q132* T133fs*26 E134* L135fs*24 F136V F136C F136S F136Y F136fs*23 V137fs*7 V137fs*22 P138R S139fs*20 N141fs*3 N141fs*18 V142fs*17 D143E G144* G144fs*14 G144fs*15 Q145H P146fs*13 F148fs*11 F148del A149fs*26 A149fs*25 A149R N150fs*9 I151T I151N I151S I151M L153fs*6 L153P P154L V155L V155M V155G V155fs*4 Y156fs*3 Y156C Y156D T157I T157TF T157fs*2 T157fs L158P L158Q L158V K159E E160* E160fs*10 E160fs E160K R161P R161G R161Q R161* C162R C162W C162Y C162F C162fs L163P L163fs*7 Q164* Q164P Q164H Q164R V166G V166D V166F R167W R167G R167Q R167fs*3 S168fs*2 L169P V170D V170F V170G K171N P172fs*30 N174fs*28 Y175D Y175fs*27 Y175* R176W R177* R177RLRVKPE L178P L178Q D179fs*23 I180N I180V I180fs*22 S183* L184P L184R Y185fs*17 Y185* E186K E186del D187fs*27 E186* D187_L188del L188Q L188P L188V E189K H191D P192S N193fs*22 Q195* K196fs*18 L198R R220W deletion of exon 2, deletion of exons 2 and 3 wherein * refers to a substitution by a stop codon, fs refers to a frameshift occurring at the indicated position and a stop codon appeared, fs*X refers to a frameshift occurring at the indicated position and a stop codon appeared after X amino acids and del a deletion.

M1fs*20 M1I E10G E12K S38F G39S P40S E41V E51Q A56fs*11 R58fs*9 P59fs*8 V62fs*5 V62fs*68 S65L S65* S65W S65fs*2 S68* S68P E70* S72fs*87 Q73* V74D F76del C77* N78S N78H N78I N78K S80N S80R P81S P81fs*78 R82P L85P P86H P86L P86S V87_W88del W88R W88C W88* L89R L89H L89P N90I N90fs*69 P95R Q96* Y98fs*61 Y98F Y98* P99fs*60 L101P G104fs*23

G104fs*55 R107fs*52 R108fs*51 I109N S111N S111G R113* G114R G114C G114S H115N H115Y H115fs*44 W117* W177R L118P F119L D121G D121Y D121E A122E T124fs*35 D126G L128P L128R L128fs*31 V130L N131fs*2 N131fs*28 N131fs*27 N131K Q132* T133fs*26 E134* L135fs*24 F136V F136fs*23 V137fs*7 V137fs*22 P138R S139fs*20 N141fs*3 N141fs*18 V142fs*17 G144* G144fs*14 G144fs*15 P146fs*13 F148fs*11 A149fs*26 A149fs*25 N150fs*9 I151T I151N I151S I151M L153fs*6 L153P P154L V155L V155M V155fs*4 Y156fs*3 T157I T157s*2 L158P L158Q L158V E160* E160fs*10 E160K R161P R161* C162R C162W C162Y C162F L163P L163fs*7 Q164* Q164P V166G V166D R167W R167Q R167fs*3 S168fs*2 L169P K171N P172fs*30 N174fs*28 Y175D Y175fs*27 Y175* R177* D179fs*23 I180N I180fs*22 L184P Y185fs*17 Y185* D187fs*27 S183* E186* D187_L188del L188Q L188P E189K N193fs*22 Q195* K196fs*18 R220W wherein * refers to a substitution by a stop codon, fs*X refers to a frameshift occurring at the indicated position and a stop codon appeared after X amino acids and del a deletion.

In one embodiment, the mutation of VHL gene is selected from those disclosed in Table 3. In particular, the mutation of VHL can be selected from the group consisting of C77fs, N131K, L118-F119 deletion, S72P, P86fs, R108fs, Q96*, I75fs, S78fs, E160fs, T157fs, N90fs, C162fs, M54fs, R167Q, L89H, L85P, W117C, L89P, and Q73*, and more specifically from the group consisting of N131K, R108fs, Q96*, E160fs, T157fs, N90fs, R167Q, L89H, L85P, W117C, L89P, and Q73*.

In a preferred embodiment, the mutation of VHL gene can be selected from the group consisting of S183* and L163P.

The loss of function of the VHL gene can be determined by several methods well known from the man skilled in the art. In particular, the loss of function of the VHL gene can be determined by measuring the activity of the VHL protein, by measuring the molecular weight of the VHL protein, by measuring the expression level of the VHL gene, and/or by detecting the presence or the absence of mutations in VHL genes. The loss of function of the VHL gene can also be determined by a combination of two or more of the methods listed above.

In one embodiment, the loss of function of the VHL gene can be determined by measuring the activity of the VHL protein. The VHL protein is an E3 ligase which has the HIF (Hypoxia Inducible Factor) transcription factor as a substrate. From a cellular extract from the sample, the E3 ligase activity of the VHL protein can be measured, for example, by a classical enzyme test. In particular, a test using a fluorescent substrate. A complete abolition of the VHL protein ligase activity or a reduction of said activity are indicative of a loss of function of the VHL gene. Preferably, a reduction of at least 10%, more preferably a reduction of at least 20%, 30%, 40%, 50% of the VHL protein ligase activity is indicative of a loss of function of the VHL gene. The degree of reduction of the VHL protein ligase activity may be determined by comparing to a reference activity value. In particular, the reference activity value can be the VHL protein ligase activity of a normal sample. The reference activity value can be an average of the activities obtained with different normal samples from different subjects.

In another embodiment, the loss of function of the VHL gene can be determined by measuring the molecular weight of the VHL protein. The normal molecular weight of the VHL protein is of 25.4 kDa. A molecular weight of the VHL protein in the sample of the patient different from 25.4 kDa is indicative of a loss of function of the VHL gene. When the fraction of the VHL proteins of the sample from the patient having a molecular weight of 25.4 kDa is reduced, it is also indicative of a loss of function of the VHL gene. For example, when the fraction of the VHL proteins having a molecular weight of 25.4 kDa is under at least 90% of the total VHL protein, preferably under 80%, 70%, 60%, 50% of the total VHL protein, it is indicative of a loss of function of the VHL gene. The molecular weight of the VHL protein can be detected by western blot or by any other classical method well known from the man skilled in the art.

In yet another embodiment, the loss of function of the VHL gene can also be determined by measuring the expression level of the VHL gene. The expression level of the VHL gene can be detected by measuring the quantity of VHL mRNA or VHL protein in a sample from said patient. An expression level under a VHL gene expression reference level being indicative of a loss of function of the VHL gene. Preferably, an expression level at least 10% under, more preferably at least 20%, 30%, 40%, 50% under the VHL gene reference expression level is indicative of a loss of function of the VHL gene. The VHL gene reference expression level is the expression level of the VHL gene in a normal sample. The VHL gene reference expression level can be an average of the activities obtained with different normal samples from different subjects. The quantity of VHL mRNA can be detected by various methods well known from the skilled man such as quantitative RT-PCR (Reverse-Transcription Polymerase Chain Reaction). The quantity of VHL protein can be detected by several methods well known from the skilled man such as Elisa, western blot and mass spectrometry.

In still another embodiment, the loss of function of the VHL gene can be determined by detecting the presence or the absence of mutations in VHL genes. Mutations of both VHL alleles or a mutation of one VHL allele and the repression of the expression of the other, for instance due to a hypermethylation of the promoter, are indicative of loss of function of the VHL gene. Different types of mutations can cause a loss of function of the VHL gene, preferably germline mutations, somatic mutations, point mutation, non-sense mutations, missense mutations, deletions, insertions, amplifications, inversions. VHL gene mutations may be detected by sequencing and comparing to the non-mutated sequence.

PD-1/PD-L1 Targeting Agents

The present invention relates to cancer treatment with PD-1/PD-L1 targeting agents. The PD-1/PD-L1 targeting agent can be a molecule targeting PD-L1, a molecule targeting PD-1 or a molecule targeting the PD-1/PD-L1 complex. Preferably, the PD-1/PD-L1 targeting agent is a molecule targeting PD-1 or the PD-1/PD-L1 complex. More preferably, the PD-1/PD-L1 targeting agent is a PD-1 antagonist or a PD-1/PD-L1 antagonist.

"PD-1 antagonist" or "PD-1/PDL-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 (Programmed cell death protein 1) and its ligands include: PDCD1, PD1, CD279 and SLEB2 for PD-1; PDCD1L1, PDL1, B7H1, B7-4, CD274 and B7-H for PD-L1 (Programmed death-ligand 1); and PDCD1L2, PDL2, B7-DC, Btdc and CD273 for PD-L2 (Programmed death-ligand 2). In any of the various aspects and embodiments of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP 054862 and NP_079515, respectively.

PD-1 antagonists useful in the any of the various aspects and embodiments of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the various aspects and embodiments of the present invention, are described in U.S. Pat. No. 7,521,051, U.S. Pat. No. 8,008,449, and U.S. Pat. No. 8,354,509. Specific anti-human PD-1 mAbs useful as the PD-1 antagonist in the various aspects and embodiments of the present invention include: MK-3475, a humanized IgG4 mAb with the structure described in WHO Drug Information, Vol. 27, No. 2, pages 161-162 (2013) and which comprises the heavy and light chain amino acid sequences shown in FIG. 6, nivolumab (BMS-936558), a human IgG4 mAb with the structure described in WHO Drug Information, Vol. 27, No. 1, pages 68-69 (2013) and which comprises the heavy and light chain amino acid sequences shown in FIG. 7; pidilizumab (CT-01 1, also known as hBAT or liBAT-1); and the humanized antibodies h409A1 1, h409A16 and h409A17, which are described in WO2008/156712.

Examples of mAbs that bind to human PD-L1, and useful in any of the various aspects and embodiments of the present invention, are described in WO2013/019906, W02010/077634 A1 and U.S. Pat. No. 8,383,796. Specific anti-human PD-L1 mAbs useful as the PD-L1 antagonist in the various aspects and embodiments of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the various aspects and embodiments of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesin molecules that specifically bind to PD-1 are described in WO2010/027827 and WO2011/066342. Specific fusion proteins useful as the PD-1 antagonist in the treatment method, compositions and uses of the present invention include AMP-224 (also known as B7-DCIg), which is a PD-L2-FC fusion protein and binds to human PD-1.

The PD-1 antagonist can be selected among a PD-1 modulating therapy, PD-1 inhibitor, anti-PD-1 immunotherapy, anti-PD-1 monoclonal antibody, a PD-1 ligand soluble construct, and/or AMP-224 (Amplimmune); performing protein analysis on PD-L1 to determine likely benefit or lack of benefit from a PD-L1 modulating therapy, PD-L1 inhibitor, anti-PD-L1 immunotherapy, anti-PD-L1 monoclonal antibody, BMS-936559, MPDL3280A/RG7446, and/or MEDI4736 (MedImmune).

In a preferred embodiment, the PD-1 antagonist is selected from the group consisting of Nivolumab (Opdivo, Bristol-Myers Squibb), Pembrolizumab (Keytruda, MK-3475, Merck), Pidilizumab (CT-011, Cure Tech), AMP-224 (Amplimmune/GlaxoSmith Klien), AMP-514 (Amplimmune/GlaxoSmith Klien), BMS 936559 (Bristol Myers Squibb), MPDL3280A (Atezolizumab, Roche), Durvalumab (MPDLI4736, MedImmune/AstraZeneca), Avelumab (MSB0010718C, Merck Serono/Pfizer) and a combination thereof, preferably from the group consisting of Nivolumab (Opdivo, Bristol-Myers Squibb), Pembrolizumab (Keytruda, MK-3475, Merck), Pidilizumab (CT-011, Cure Tech), BMS 936559 (Bristol Myers Squibb), MPDL3280A (Roche), RG7446 (Genentech—Hoffmann-La Roche), MEDI4736 (AstraZeneca) AMP-514 (MedImmune) and AMP-224 (GlaxoSmithKline).

In a most preferred embodiment, the PD-1 antagonist is selected from the group consisting of Nivolumab (Opdivo, Bristol-Myers Squibb), Pembrolizumab (Keytruda, MK-3475, Merck), Pidilizumab (CT-011, Cure Tech), BMS 936559 (Bristol Myers Squibb), and MPDL3280A (Roche).

Treatment

In yet another aspect, the present method further comprises a step of treating the patient with a loss of function of the VHL gene.

The treatment of the patient having a loss of function of the VHL gene may comprise the administration to the patient of an effective amount of a therapeutic agent, preferably a PD-1/PD-L1 agent.

It is understood that the administered dose of the therapeutic agent may be adapted by those skilled in the art according to the patient, the pathology, the mode of administration, etc. The dosage and regimen depends in particular on the stage and severity of the prostate cancer, the weight and general state of health of the patient and the judgment of the prescribing physician.

The invention also relates to a method of identifying a patient who may benefit from treatment with an immunotherapy that includes blockade of PD-1 signaling comprising the steps of:

(a) detecting if cells from a sample from said patient present or not a loss of function of the von Hippel-Lindau (VHL) gene, wherein the loss of function of the VHL gene indicates that the patient will benefit from treatment with an immunotherapy that includes blockade of PD-1 signaling, and (b) selecting patients with loss of function of the VHL gene as suitable for a treatment with an immunotherapy that includes blockade of PD-1 signaling.

This method may further comprise a step of treating the patient with a loss of function of the VHL gene.

In another aspect of the invention, the invention relates to an in vitro or ex vivo method for selecting a patient affected with a tumor for not having a treatment with a PD-1/PD-L1 targeting agent, wherein the method comprises:

(a) detecting if cells from a sample from said patient present or not a loss of function of the von Hippel-Lindau (VHL) gene, wherein the absence of loss of function of the VHL gene is predictive of the non-responsiveness of said patient to a treatment with a PD-1/PD-L1 targeting agent, and (b) selecting patients with the absence of loss of function of the VHL gene as non-suitable for a treatment with a PD-1/PD-L1 targeting agent.

In still another aspect, the invention relates to the use of the loss of function of the VHL gene as a biomarker for selecting a patient affected with a tumor for a treatment with a PD-1/PD-L1 targeting agent.

Kit and Use of a Kit

In yet another aspect of the invention, the invention relates to a kit for selecting a patient affected with a tumor for a treatment with a PD-1/PD-L1 targeting agent, wherein the kit comprises means for the detection of the loss of function of the VHL gene selected from the group consisting of a pair of primers targeting the VHL gene, primers targeting the VHL mRNA, a pair of primers targeting the VHL cDNA, a probe targeting the VHL cDNA, a probe targeting the VHL mRNA, a probe targeting the VHL DNA, a VHL substrate, an antibody specific of the VHL protein, and a combination thereof.

In a preferred embodiment of the above mentioned kit, the kit may comprise means for the detection of the activity of the VHL protein, for example a VHL substrate suitable for an enzyme test, more preferably a VHL fluorescent substrate, even more preferably a substrate that fluoresce after being processed by the VHL protein or a substrate which fluorescence is modified by the activity of the VHL protein. In a particular embodiment the substrate is related to the HIF protein.

In another preferred embodiment of the above mentioned kit, the kit may comprise means for the detection of the molecular weight of the VHL protein, for example a VHL specific antibody suitable for a western blot method.

In still another preferred embodiment of the above mentioned kit, the kit may comprise means for the detection of the expression level of the VHL gene, preferably means for measuring the amount of the VHL mRNA and/or means for measuring the amount of the VHL protein. In particular, the kit may comprise means for measuring the amount of the VHL mRNA such as primers targeting the VHL mRNA suitable for the reverse transcription of the VHL mRNA in cDNA, and a pair of primers targeting the VHL cDNA suitable for quantitative PCR, and/or a VHL cDNA probe suitable for quantitative PCR. Alternatively, the kit may also comprise means for measuring the amount of the VHL protein, such as antibodies specific of the VHL protein suitable for western blot or Elisa methods.

In yet another preferred embodiment of the above mentioned kit, the kit may comprise means for the detection of the presence of mutations of the VHL gene such as a pair of primers targeting the VHL gene suitable for the VHL gene sequencing or a probe targeting the VHL DNA suitable for identification of known mutations of the VHL gene.

Optionally, the above mentioned kit further comprises a leaflet providing guidelines to use such a kit.

In another aspect of the invention, the invention relates to the use of a kit for selecting a patient affected with a tumor for a treatment with a PD-1/PD-L1 targeting agent, wherein the kit comprises means for the detection of the loss of function of the VHL gene selected from the group consisting of primers targeting the VHL gene, a pair of primers targeting the VHL mRNA, a pair of primers targeting the VHL cDNA, a probe targeting the VHL cDNA, a probe targeting the VHL mRNA, a probe targeting the VHL DNA, a VHL substrate, an antibody specific of the VHL protein, and a combination thereof.

Box plots represent the distribution of PD-L1 mRNA expression (average fold change) according to VHL mutation status for the different classifications: (A) Loss of heterozygosity (LOH) (presence of LOH=1, absence of LOH=0), (B) Number of altered alleles (1 corresponding to 0 and 1 altered allele), (C) Loss of function (presence of LOF=1, absence of LOF=0). (n=32).

Figure 2:
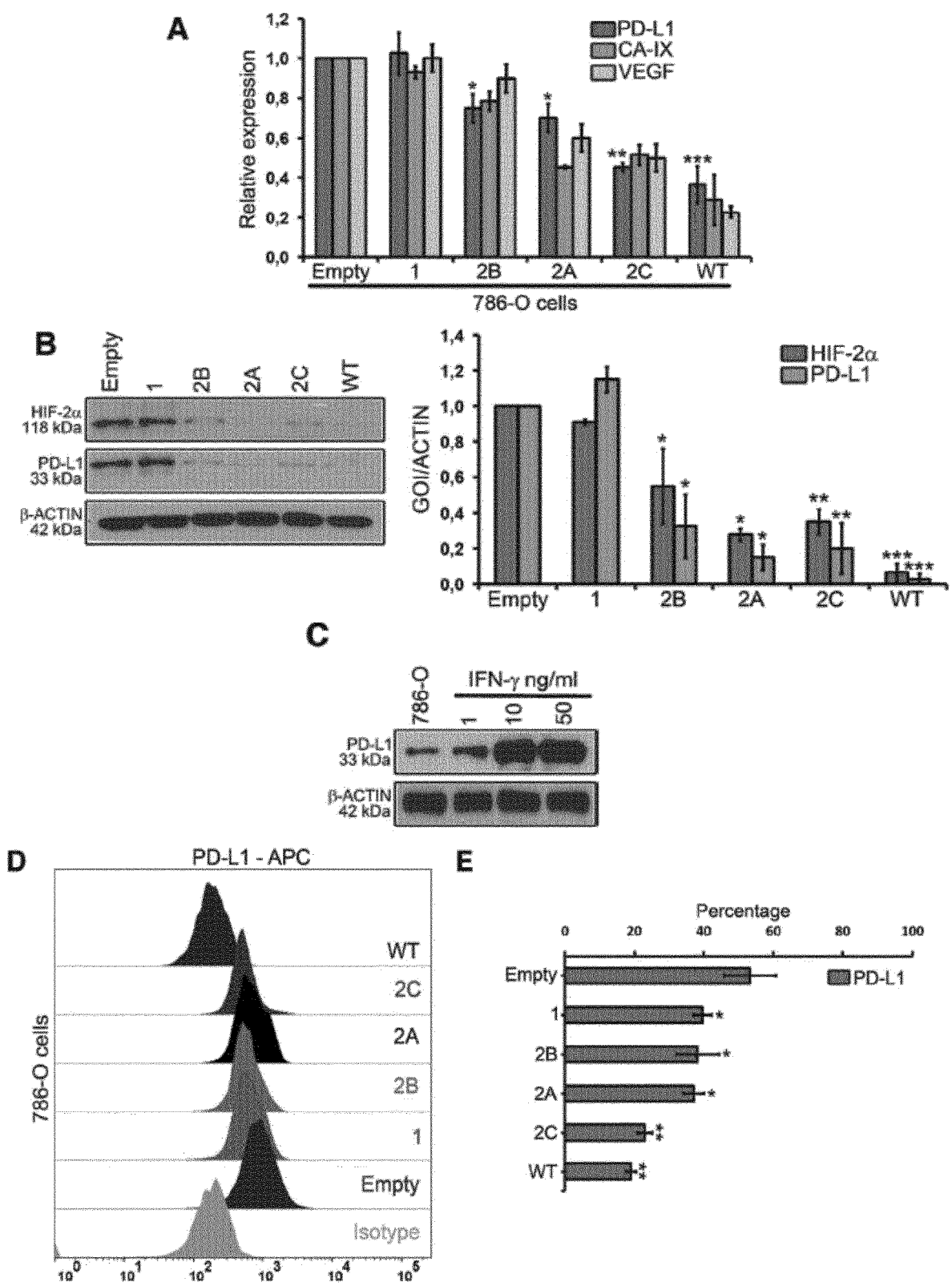

FIG. 2. Differential PD-L1 Expression in 786-O Cells Transfected with Different VHL Mutants.

(A) PD-L1, CA-IX and VEGF expression were evaluated by SYBR-GREEN qRT-PCR. (B) Western blot was performed to show HIF-2α, and PD-L1 protein levels. Actin was used as a loading control. (C) 786-O cells were incubated with interferon gamma (IFN-γ) for 24 hours. Western blot was performed to show PD-L1 protein levels. Actin was used as a loading control. (D and E) Surface expression levels of PD-L1 and PD-L2 were determined by flow cytometry. Data represent 3 independent experiments with standard deviation (SD). Statistically significant difference (indicated by asterisks) between WT cells and different VHL mutants are shown (*=P<0.05, =P<0.005 and *=P<0.0005).

Figure 3:
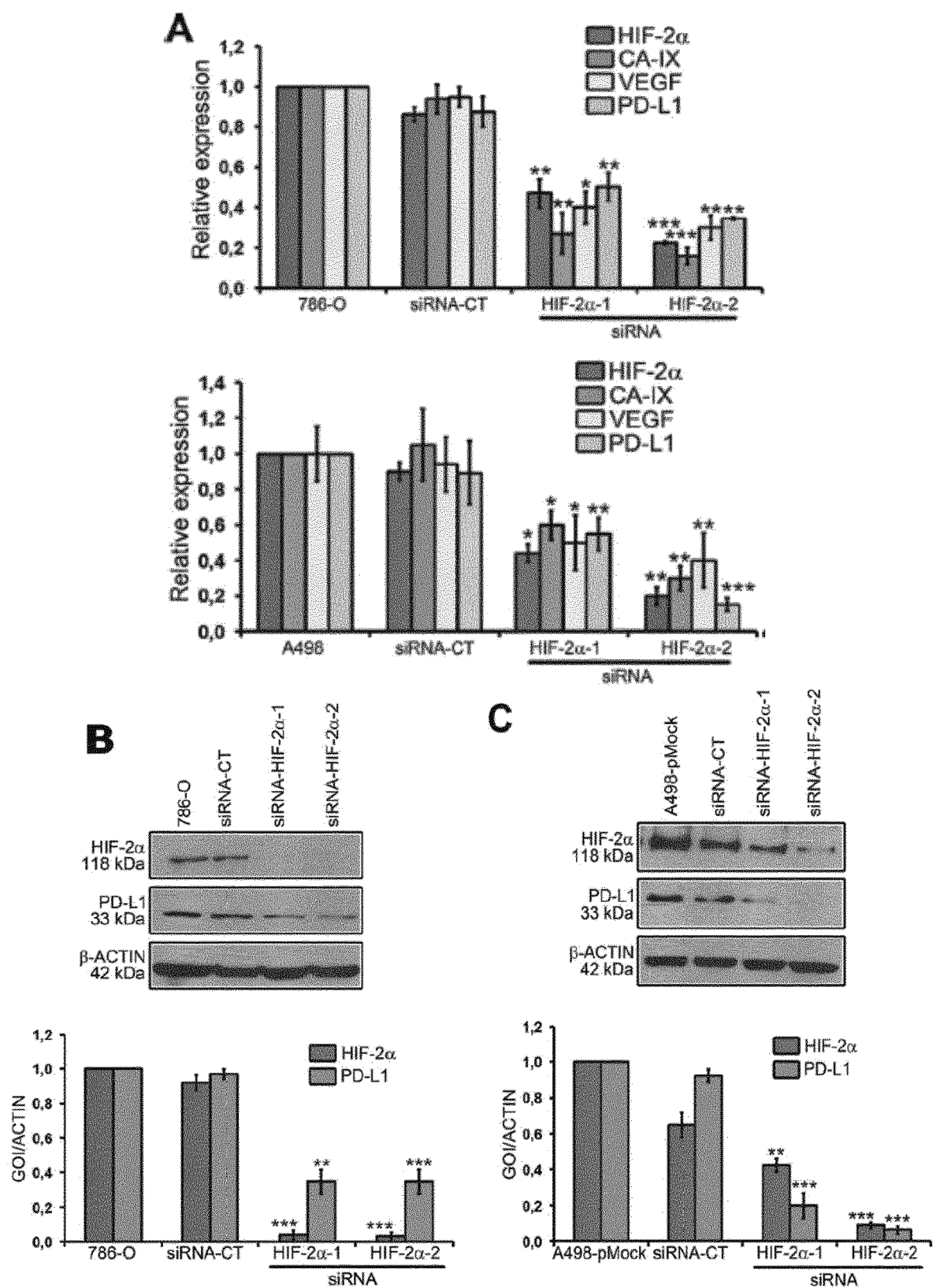

FIG. 3. HIF-2α Silencing Decreased PD-L1 Expression in 786-O and A498 Cells.

786-O and A498 cells were transfected with 2 different siRNAs targeting HIF-2α or scrambled control (CT). (A) Expression levels of HIF-2α, CA-IX, VEGF and PD-L1 were evaluated by SYBR-GREEN qRT-PCR. (B and C) Western blot was performed to show HIF-2α and PD-L1 protein levels in 786-O (B) and A498 (C) cells. Actin was used as a loading control. (D and E) Surface expression levels of PD-L1 in 786-O (D) and A498 (E) cells were determined by flow cytometry. Data represent 3 independent experiments with SD. Statistically significant difference (indicated by asterisks) between cells transfected with siRNA targeting scrambled control or HIF-2α are shown (*=P<0.05, =P<0.005 and *=P<0.0005).

Figure 4:
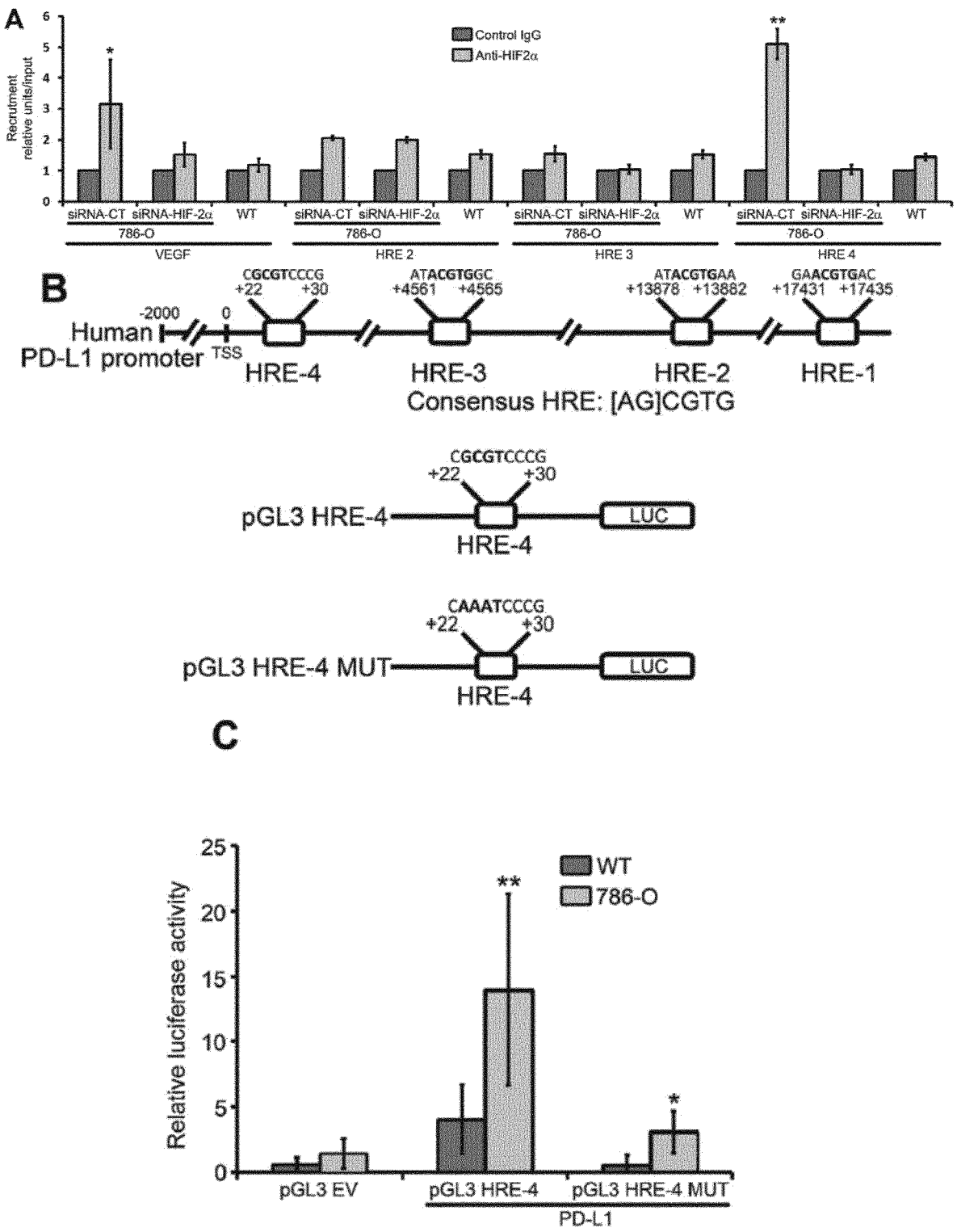

FIG. 4. HIF-2 Regulates the Expression of PD-L1 by Binding Directly to the HRE-4 in the PD-L1 Proximal Promoter in 786-O Cells (A) ChIP assay was performed on 786-O cells transfected with either siRNA against HIF-2α or scrambled control (CT) and on WT cells using anti-HIF-2α antibody followed by SYBR-GREEN RT-qPCR using VEGFA and PD-L1 HRE sites. (B) Different Hypoxia Response Elements (HRE) in human PD-L1 promoter are shown. (C) 786-O and WT cells were co-transfected with pGL4-hRluc/SV40 vector and pGL3 empty vector (pGL3 EV), pGL3 HRE-4 or pGL3 HRE-4 MUT vectors. After 48 h, firefly and *Renilla* luciferase activities were measured using the Dual-Luciferase Reporter assay (Promega) and the ratio of firefly:*Renilla* luciferase was determined. Data represent 3 independent experiments with SD. Statistically significant difference (indicated by asterisks) are shown (*=P<0.05, =P<0.005 and *=P<0.0005).

(D) WT (wild type VHL) cells were transfected with a pcDNA3 EV or pcDNA3-HIF-2α (3 µg and 5 µg). HIF-2α expression was detected by western blot. Actin was used as a loading control. (E) Surface expression levels of PD-L1 was determined by flow cytometry. Data represent 3 independent experiments with SD. Statistically significant difference (indicated by asterisks) between cells transfected with pcDNA3 EV pcDNA3-HIF-2α are shown (*=P<0.05, =P<0.005 and *=P<0.0005).

(F-H) HIF-1α and HIF-2α regulate PD-L1 expression in RCC4 cell line. RCC4 cells were transfected with siRNAs targeting HIF-1α, HIF-2α, both HIF-1α and HIF-2α or scrambled control (CT). (F) Expression levels of VEGF and PD-L1 were evaluated by SYBR-GREEN qRT-PCR. (G) Western blot was performed to show HIF-1α, HIF-2α and PD-L1 protein levels in RCC4. Actin was used as a loading control. (H) Surface expression levels of PD-L1 in RCC4 were determined by flow cytometry. The graph represents percentage of positive cells. Data represent 2 independent experiments with SD. Statistically significant difference (indicated by asterisks) between cells transfected with siRNA targeting scrambled control or HIF-1α, HIF-2α and HIF-1α+HIF-2α are shown (*=P<0.05, =P<0.005 and *=P<0.0005).

Figure 5:
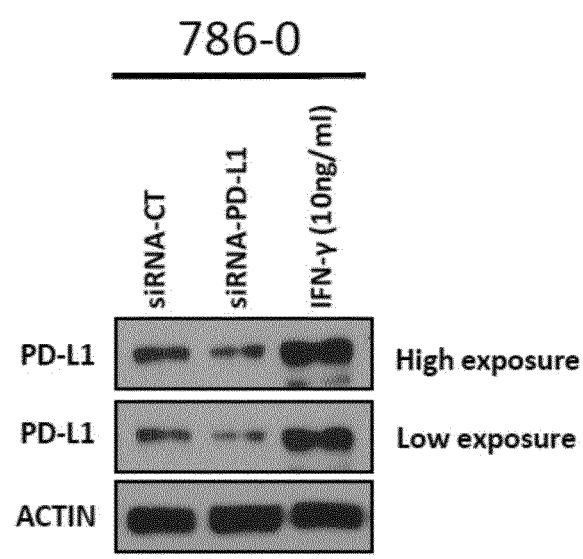

FIG. 5. PD-L1 Overexpression and Silencing in 786.O.

786.O cells were transfected with siRNAs targeting HIF-2α, scrambled control or incubated with IFN-gamma (24 h). Western blot was performed to show PD-L1 protein levels in 786.O cells. Actin was used as a loading control.

EXAMPLES

Introduction

Clear cell renal cell carcinomas (ccRCC) account for approximately 3% of adult cancers [1]. Loss of function of the von Hippel-Lindau (VHL) tumor suppressor gene occurs in VHL disease [2]. VHL can be altered by germline or somatic mutations together with loss of heterozygosity (LOH) or promoter hypermethylation [3]. Damaging VHL mutations include those where the functional consequence is a truncated VHL protein (pVHL) (caused by nonsense, frame shift mutations or certain defaults of the splice sites) or partial wild-type VHL function (caused by missense mutations and in-frame deletions) [4, 5]. Thus, biallelic inactivation of the VHL gene (with no wild-type remaining copy) is defined as the association of a damaging mutation (germline or somatic) either with LOH or promoter hypermethylation, which leads to a complete loss-of-function (LOF) of the pVHL.

VHL is reported to be altered in 70-90% of sporadic ccRCC [6, 7]. Loss of VHL function in ccRCC leads to the constitutive stabilization of hypoxia-inducible factors (HIFs), in particular HIF-2α [8], resulting in highly angiogenic environment in these extremely vascularized and chemo-radio-resistant ccRCC [9].

Recent preclinical and clinical data indicate that antibody blockade of immune checkpoints can enhance antitumor immunity [10]. In this regard, aberrant programmed death-ligand 1 (PD-L1) expression has been reported in several human cancers including RCC [11]. The inventors have recently shown that hypoxia via HIF-1α can directly up-regulate PD-L1 expression in various tumor cells (melanoma, lung cancer and breast cancer) as well as macrophages, dendritic cells (DC) and myeloid derived suppressor cells (MDSC) [12].

Several studies have described a positive correlation between PD-L1 expression, metastasis, and poor outcome in ccRCC [13]. Recently, antibody-mediated blockade of PD-1 [14] and PD-L1 [15] was shown to result in durable tumor regression and prolonged stabilization of disease in patients with advanced cancer including RCC [16].

Although frequent VHL loss of function (LOF) is a critical factor in RCC progression, the association between VHL mutation status and immune checkpoint PD-L1 expression remains unknown. Our main objective was to elucidate the putative relationship between VHL mutations and PD-L1 expression. In the present study, the inventors showed that VHL mutation status significantly correlated with PD-L1 expression in ccRCC patients. They also demonstrated that VHL mutations induced-HIF-2α stabilization positively regulates PD-L1 expression.

Results

Loss of Function of the VHL Gene is Associated with PD-L1 Expression in ccRCC ccRCC patients were characterized for the VHL mutation status of both alleles, including a search for somatic point mutations, LOH, and hypermethylation of the VHL promoter (Table 3). Among this series, 59.4% were male, 65.6% with sporadic (spo) ccRCC, (6.3%/46.9%) with grade 1-2 and (28.1%/21.9%) with stage 1-2 (Table 1).

The tumors were first classified according to the type of VHL alterations, i.e., presence of LOH in 3p25 (C1) and number of altered alleles (C2) based on the count of gene copies (i.e. 0, 1 or 2). Secondly, an assessment of LOF was made based on the damaging status corresponding to the precise type of the VHL mutations (probably damaging: a complete loss of both alleles; benign: both alleles are wild-type; possibly damaging: other cases , Table 3) and the presence of LOH or promoter hypermethylation (C3). Using these criteria, 71.9% of tumors presented LOH, 65.6% had 2 VHL altered alleles and 43.8% had LOF for VHL (Table 1).

The expression of PD-L1 was then evaluated by qRT-PCR on these 32 ccRCC (Table S1 and FIG. 1A). We observed a statistically significant association between VHL status and PD-L1 expression, regardless of our criteria for VHL classification. Indeed, the median of PD-L1 expression for tumors presenting with LOH (5.1 [4.8-6.3]) was significantly higher as compared to ccRCC with absence of LOH (2.7 [2.1-4.3]; FIG. 1A; p=0.0001). Furthermore, the median of PD-L1 expression in tumors with 2 altered alleles (5.2; 95% CI=[4.8-6.3]) was significantly higher than that in tumors with 0 or 1 altered allele (FIG. 1B; 2.9 [2.6-4.5]; p<0.0001). Similar results were obtained for tumors with VHL LOF (5.4 [4.8-6.3]) versus tumors with no LOF (4.4 [2.7-4.8]; FIG. 1C; p=0.025).

Figure 1:
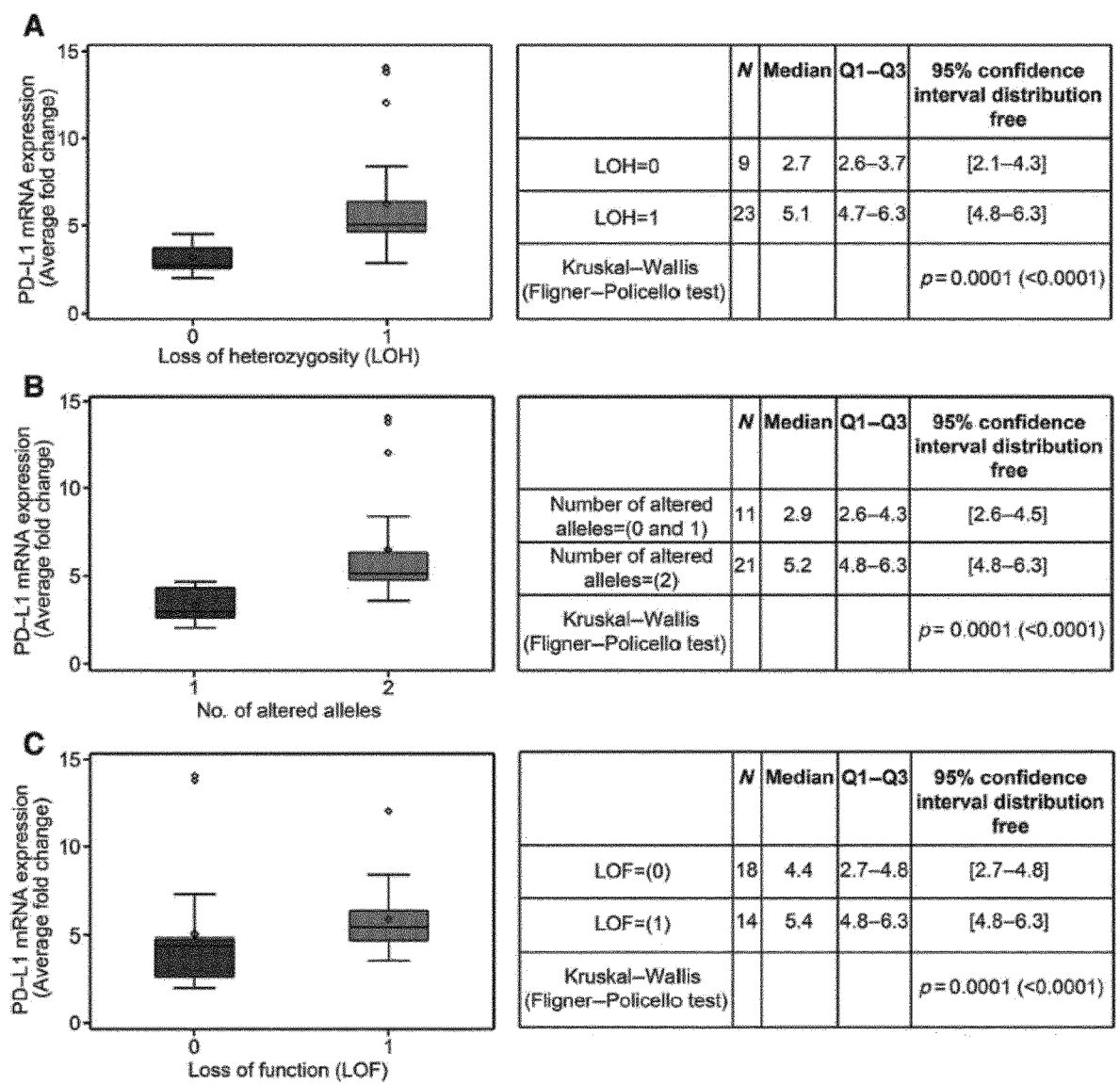
FIG. 1. VHL Mutation Status is Associated with PD-L1 Expression in ccRCC

The Gradient Expression Levels of HIF-2α Positively Correlated with PD-L1 Expression We next used different VHL mutants obtained by reintroduction of six different VHL transfects in the VHL-defective 786-O cell line overexpressing only HIF-2α. In these VHL mutant cells, gradual pVHL LOF induces a gradual dysregulation of HIF-2α expression [5]. We compared the level of expression of PD-L1 in these six ccRCC VHL mutant cell lines (empty, 1, 2B, 2A, 2C) and WT cells (transfected with wild type VHL). The results revealed that VHL mutant cells with different gradient expression levels of HIF-2α positively correlated with PD-L1 expression at both mRNA and protein levels (FIGS. 2A and 2B). As shown in FIG. 2C, IFN-γ treated 786-O cells was used as a positive control and siRNA-mediated silencing of PD-L1 in 786-O cells (and FIG. 5) was used as a negative control for the detection of PD-L1 (33 kDa) by western blot. Similarly, as shown in FIGS. 2D and 2E, surface expression of PD-L1 was significantly decreased in VHL mutants (1, 2B, 2A, 2C) as compared to cells transfected with empty vector (786-O cells). More importantly, PD-L1 was significantly decreased in WT cells (transfected with wild type VHL) as compared to empty (786-O) cells (FIG. 2A-2E). These data point to the existence of a correlation between VHL mutations and PD-L1 expression in 786-O cell line, confirming our data on ccRCC tumors (FIG. 1).

Targeting HIF-2α Resulted in a Decrease in PD-L1 Expression in ccRCC Cells

To determine whether the correlation between VHL mutation status and PD-L1 expression involves HIF-2α, we knocked down HIF-2α using siRNA in pVHL defective 786-O and A498 ccRCC cell lines. Remarkably, siRNA-mediated knockdown of HIF-2α significantly decreased PD-L1 mRNA and protein expression levels in both 786-O (FIGS. 3A and 3B) and A498 (FIGS. 3A and 3C) cells. Similarly, the surface expression of PD-L1 was significantly decreased in both 786-O (FIG. 3D) and A498 (FIG. 3E) cells transfected with siRNA targeting HIF-2α.

HIF-2 Regulates the Expression of PD-L1 by Binding Directly to the HRE in the PD-L1 Proximal Promoter in 786-O Cells To gain insight into the mechanism by which HIF-2α regulates PDL1 expression, we first searched for potential HIF-2α binding sites in the proximal promoter of human PD-L1 gene using fuzznuc (EMBOSS explorer) software. As depicted in FIGS. 4A and 4B, we found putative hypoxia response elements (HREs) containing the consensus sequence (A/G) CGTG within the human PD-L1 gene. Using chromatin immunoprecipitation (ChIP), we demonstrated specific binding of HIF-2α only at HRE-4 on the PD-L1 promoter in 786-O cells but not in 786-O transfected with siRNA HIF-2α or in the VHL-corrected WT cell line (FIG. 4A). ChIP complexes in 786-O cells showed a significant binding of HIF-2α at HRE-4 (>4 fold), comparable to their binding to an established HRE in VEGF gene.

To determine whether this HIF-2α site (HRE-4) was a transcriptionally active HRE, 786-O cells were co-transfected with pGL4-hRluc/SV40 vector and pGL3 HRE-4, or pGL3 HRE-4 MUT vectors. Firefly and *Renilla* luciferase activities were measured. As shown in FIG. 4C, 786-O cells increased the luciferase activity of HRE-4 reporter by more than threefold as compared with VHL-corrected-WT cell line. More interestingly, the luciferase activity of HRE-4 MUT was significantly decreased as compared with HRE-4 in 786-O cells. Moreover, overexpression of HIF-2α in WT cells (transfected with wild type VHL) resulted in a significant increase in PD-L1 expression levels as detected by western blot (FIG. 4D) and flow cytometry (FIG. 4E).

In order to determine whether HIF-1α also regulates PD-L1 in ccRCC cells, we used VHL-mutated RCC4 cell line expressing both HIF-1 and HIF-2. As shown in FIG. 4F-H, the knock-down of HIF-1, HIF-2 or both the HIF-1 and HIF-2 induced significant decrease in both PD-L1 mRNA (4F) and protein expression (4G and 4H).

The results presented in FIG. 4 demonstrate that PD-L1 is a novel direct HIF-2α target gene in 786-O cells and both HIF-1α and HIF-2α regulate PD-L1 expression in RCC4 cells. Thus, we provide evidence here that HIF-2α is a critical regulator of PD-L1 at both mRNA and protein levels and that HIF-2α regulates the expression of PD-L1 by binding directly to the HRE-4 in the PD-L1 proximal promoter.

Discussion

We first demonstrated that loss of function of the VHL gene is associated with PD-L1 expression in ccRCC patients. It has been reported that depending on the VHL mutation type, some functions of the pVHL could be maintained [4, 5]. Our work is the first to demonstrate that LOF of the VHL gene is associated with a significant increase in PD-L1 expression in ccRCC tumors. Although classification of the VHL status based on biallelic inactivation and the type of the mutation (i.e. probably or less damaging) is not a standard approach, all retained criteria showed statistically significant higher expression of PD-L1 in ccRCC patients presenting VHL loss of function. The involvement of other factors (sex, grade, stage) is ruled out (data not shown).

While VHL mutations were reported to play a significant roles in ccRCC development [19, 20], their role in modulating the immune response remains largely unknown. Recently, we demonstrated that VHL mutations decreased RCC cell susceptibility to NK-mediated lysis via HIF-2α stabilization [17]. Here we provide evidence for the existence of a new link between the VHL gene, altered in the majority of ccRCC tumors, and the immune checkpoint PD-L1 expression.

The molecular mechanisms underlying the regulation of PD-L1 expression in RCC are not well established. Recently, it was shown that both c-Met and PD-L1 are overexpressed and co-localized in human renal cancer tissues; and pharmacological induction of c-Met up-regulated PD-L1 expression, which was prevented following treatment with pharmacological inhibitors of c-Met in RCC cells [21]. In fact, accumulating evidence indicate that HIF-2α is important for ccRCC development and progression [22, 23]. In the ccRCC cell lines used in this study (786-O and A498 cells), VHL mutation selectively induces HIF-2α stabilization (and not HIF-1α), thus representing an ideal model to specifically examine the specific role of HIF-2α on PD-L1 expression. Using these models (786-O and A498 cells), we showed that targeting HIF-2α attenuates PD-L1 expression and that that PD-L1 is a novel direct HIF-2α target gene in 786-O cells.

Several tumor microenvironmental factors such as Interferon gamma (IFN-γ) [24], IL-10 and VEGF [25] have been shown to induce/up-regulate PD-L1 expression [26]. We have recently provided evidence that HIF-1α is a major regulator of PD-L1 mRNA and protein expression, and that HIF-1α regulates the expression of PD-L1 by binding directly to the HRE-4 in the murine PD-L1 proximal promoter [12]. Resistance to various anti-angiogenic therapies including sunitinib was found to be associated with an increased PD-L1 expression and an immunosuppressive tumor microenvironment [27]. Although we showed that both HIF-1α and HIF-2α regulate PD-L1 expression in VHL mutated ccRCC cells, we cannot exclude that additional mechanisms presumably contribute to PD-L1 expression in ccRCC tumors.

Immune checkpoint based immunotherapies have shown strong and long-lasting clinical responses in ccRCC [14-16]. Recently, the expression of immune checkpoints and the localization of DC in the tumor microenvironment were shown to modulate the clinical impact of CD8[+] T lymphocytes in ccRCC [28]. It is tempting to speculate that the VHL mutation status may be a potential predictive marker candidate for RCC anti-PD-L1/PD-1 immunotherapy. PD-1/PD-L1 blockade, future experiments should answer this intriguing question. It would be of interest to investigate the effect of anti-PD-1 treatment on tumor growth and tumor immune infiltrate of VHL mutated and VHL wild type Renca RCC xenografts. In addition, a better understanding of the interplay between angiogenesis and PD-1 axis in RCC, has the potential to develop clinical trial of dual inhibition or define the optimal sequence for VEGF/VEGFR targeting and PD-1/PD-L1 inhibition in metastatic RCC patients.

Conclusions

The present data provide insight into the link between VHL mutations, the HIF-2α-related pathway, and PD-L1 expression, and point to a critical role of VHL/HIF-2α axis in controlling anti PD-L1 response.

Materials and Methods

Tumor Tissue Samples

A series of 32 renal tumors, composed of 11 VHL tumor-associated and 21 sporadic RCC verified as being clear-cell renal cell carcinomas, with tumor cell content of at least 60%, was obtained thanks to the French Kidney Cancer Consortium (Table 1). Matched normal renal tissue was available for 13 of the 21 sporadic cases. This study was approved by the Ethics Committee of Le Kremlin-Bicêtre University Hospital, France. All patients had provided informed consent before surgery for use of their tumors for further investigations.

The association between VHL mutation and PD-L1 expression was tested using the Fisher's exact test for VHL mutation and the Kruskal-Wallis test for PD-L1 expression. If no covariate accounted for the association of VHL and PD-L1, then a Kruskal-Wallis test was used; otherwise we used the Cochran-Mantel-Haenszel test. The distribution of PD-L1 markers across mutation type was described by histogram, box plot and median [Q1-Q3], and distribution free confidence interval. We also used the Fligner-Policello test used to compare 2 medians when the distributions had different dispersion.

VHL Mutation Status, LOH and Promoter Methylation Analysis on Tumor DNA

The three exons and exon-intron junctions of the VHL gene were sequenced on DNA extracted from tumor samples, as previously described [5]. Search for LOH was performed by Multiplex PCR (Qiagen Master Mix) using forward primers coupled with fluorescent dye designed for 6 microsatellite markers spreading across a 4.6 Mb region surrounding the VHL gene in 3p25-26. Fluorescent data were analyzed by GeneMapper software, and peak intensity ratios were calculated by Microsoft Excel using either germline or matched renal normal DNA compared to tumor DNAs. Methylation status of the VHL promoter was studied by digestion with NotI followed by semi-quantitative PCR of the exon 1 using fluorescent primer. Analysis was performed as a LOH study.

Cell Lines

The 786-O and A498 cell lines were obtained from Dr. William Kaelin, Jr. (Dana Farber Institute, Harvard Medical School, Boston, Mass.). Both 786-O and A498 cells have a frameshift mutation in the VHL gene associated with a LOH. The 786-O cells were transduced by different non-tagged VHL-inducible lentiviral constructs and maintained in selective medium: as described previously [5].

SYBR Green Real-Time Quantitative PCR (qRT-PCR)

SYBR Green RT-qPCR was performed as described previously [12]. 18S was used as housekeeping gene. Primers sequences are detailed in Table 2.

Western Blot

Western blotting was conducted as previously reported [17]. Anti-HIF-2α and anti-PD-L1 antibodies were purchased respectively from Novus Biotechnology (NB-100-122) and Abcam (ab-58810). Predesigned siRNA against HIF-2α and scrambled control were obtained from Ambion and transfected by electroporation as described previously [17].

Flow Cytometry Analysis

Flow cytometry was performed using a FACS LSR-II (BD). Data were further analyzed by FACS DIVA 7.0 (BD) or Flow Jo 7.6.5 software (Tree Star). Anti-PD-L1-APC and control antibody (Isotype-APC) were purchased from Biolegend. Percentage refers to percentage of live positive cells.

ChIP (Chromatin Immunoprecipitation) Assay

ChIP assay was performed as described [18]. Primers sequences are detailed in Table 2.

Statistical Analysis

Data were analyzed with GraphPad Prism. Student's t-test was used for single comparisons.

REFERENCES

[1] Gupta K, et al. Cancer treatment reviews. 2008; 34:193-205.

[2] Latif F, et al. Science. 1993; 260:1317-20.

[3] Gnarra J R, et al. Nature genetics. 1994;7:85-90.

[4] Rechsteiner M P, et al. Cancer research. 2011; 71:5500-11.

[5] Couve S, et al. Cancer research. 2014; 74:6554-64.

[6] Young A C, et al. Clinical cancer research: an official journal of the American Association for Cancer Research. 2009;15:7582-92.

[7] Sato Y, et al. Nature genetics. 2013; 45:860-7.

[8] Kaelin W G, et al. Nature reviews Cancer. 2008; 8:865-73.

[9] Escudier B, et al. Clinical genitourinary cancer. 2014; 12:1-12.

[10] Pardoll D M. Nature reviews Cancer. 2012; 12:252-64.

[11] Wu P, et al. PloS one. 2015; 10:e0131403.

[12] Noman M Z, et al. The Journal of experimental medicine. 2014; 211:781-90.

[13] Thompson R H, et al. Clinical cancer research: an official journal of the American Association for Cancer Research. 2007; 13:709s-15s.

[14] Topalian S L, et al. The New England journal of medicine. 2012; 366:2443-54.

[15] Brahmer J R, et al. The New England journal of medicine. 2012; 366:2455-65.

[16] Motzer R J, et al. Journal of clinical oncology: official journal of the American Society of Clinical Oncology. 2015; 33:1430-7.

[17] Messai Y, et al. Cancer research. 2014; 74:6820-32.

[18] Jacque E, et al. Oncogene. 2013; 32:2661-9.

[19] Richard S, et al. Seminars in cancer biology. 2013; 23:26-37.

[20] Maher E R, et al. European journal of human genetics: EJHG. 2011; 19:617-23.

[21] Balan M, et al. The Journal of biological chemistry. 2015; 290:8110-20.

[22] Kondo K, et al. PLoS biology. 2003; 1:E83.

[23] Gordan J D, et al. Cancer cell. 2008; 14:435-46.

[24] duPre S A, et al. Experimental and molecular pathology. 2008; 85:174-88.

[25] Curiel T J, et al. Nature medicine. 2003; 9:562-7.

[26] Topalian S L, et al. Cancer cell. 2015; 27:450-61.

[27] Liu X D, et al. Cancer immunology research. 2015.

[28] Giraldo N A, et al. Clinical cancer research: an official journal of the American Association for Cancer Research. 2015; 21:3031-40.

TABLE 1

Clinical characteristics of the 32 patients affected with clear-cell Renal Cell Carcinoma (ccRCC) and VHL alterations.

| Clinical characteristics | | % (n) |
|---|---|---|
| Sex | Female | 40.6 (13) |
|  | Male | 59.4 (19) |
| Histology | VHL ccRCC | 34.4 (11) |
|  | Sporadic ccRCC | 65.6 (21) |
| Grade | 1 | 6.3 (2) |
|  | 2 | 46.9 (15) |
|  | 3 | 34.4 (11) |
|  | 4 | 12.5 (4) |
| Stage | 1 | 28.1 (9) |
|  | 2 | 21.9 (7) |
|  | 3 | 43.8 (14) |
|  | 4 | 6.3 (2) |
| VHL alterations‡ | | |
| C1. Presence of LOH£ | 0 | 28.1 (9) |
|  | 1 | 71.9 (23) |
| C2. Number of altered alleles¶ | 0 | 3.1 (1) |
|  | 1 | 31.3 (10) |
|  | 2 | 65.6 (21) |
| C3. Presence of LOF$ | 0 | 56.3 (18) |
|  | 1 | 43.8 (14) |

‡Three classifications (C1-C3) were used. VHL alterations of each ccRCC are reported in Table 3.
£LOH = Loss of Heterozygosity. Presence = 1, absence = 0.
¶Regarding the number of tumors in the first class (n = 1), we collapsed the first and second classes for statistical analyses.
$LOF = Loss of Function, i.e. biallelic inactivation of the gene. Class 1 corresponds to the classification of mutations as "probably damaging" in Table 3, vs class 0 where "possibly damaging" and "benign" (n = 1) mutations were grouped together. Presence = 1, absence = 0.

TABLE 2

Genomic oligonucelotide primers used for amplification of immunoprecipitated DNA samples from ChIP assays.

| Primer | Sequence | SEQ ID No |
|---|---|---|
| VEGF-FWD | TCAGTTCCCTGGCAACAT | 1 |
| VEGF-REV | ACCAAGTTTGTGGAGCTGAG | 2 |
| HRE-1-PDL1-H-FWD | GGAGGAGACGTAATCCAGCA | 3 |
| HRE-1-PDL1-H-REV | ATTCTCCTCCTCTGCTTTCG | 4 |
| HRE-2-PDL1-H-FWD | TCCTCATGGGTTATGTGTAGTTTG | 5 |
| HRE-2-PDL1-H-REV | TCCCTCTTAGTGCCTCTCCA | 6 |
| HRE-3-PDL1-H-FWD | TGCACTGAGTCTGTTTCCTCA | 7 |
| HRE-3-PDL1-H-REV | CCATCTTTGACTACCCAGGTG | 8 |
| HRE-4-PDL1-H-FWD | GATTTCACCGAAGGTCAGGA | 9 |
| HRE-4-PDL1-H-REV | CTACCTGCAGGCGGACAG | 10 |

Primer sequences for SYBR Green RT-qPCR

| Primer | Sequence | SEQ ID No |
|---|---|---|
| 18S-H-FWD | CGGACAGGATTGACAGATTG | 11 |
| 18S-H-REV | CAAATCGCTCCACCAACTAA | 12 |
| HIF-2α-H-FWD | GCGCTAGACTCCGAGAACAT | 13 |
| HIF-2α-H-REV | TGGCCACTTACTACCTGACCCTT | 14 |
| VEGFA-H-FWD | GCACCCATGGCAGAAGG | 15 |
| VEGFA-H-REV | CTCGATTGGATGGCAGTAGCT | 16 |
| CAIX-H-FWD | CTGAAGACAGGATGGAGAAG | 17 |
| CAIX-H-REV | GCAGAGTGCGGCAGAATG | 18 |
| PDL1-H-FWD | TGTACCGCTGCATGATCAG | 19 |
| PDL1-H-REV | AGTTCATGTTCAGAGGTGACTG | 20 |

TABLE 3

| Sex | Histology | Fuhrman's grade | Stage | VHL status | Mutated exon | Description of mutations | Type of alterations | Presence of LOH (C1) | Nb altered alleles (C2) | Presence LOF (C3) |
|---|---|---|---|---|---|---|---|---|---|---|
| M | sporadic ccRCC | 3 | 3a | wild-type | / | / | / | 0 | 0 | 0 |
| M | sporadic ccRCC | 3 | 2a | mutated | 1 | c.230_231insTGC, p.Cys77fs | frameshift | 0 | 1 | 0 |
| M | sporadic ccRCC | 2 | 3b | mutated | 2 | c.391C > G, p.Asn131Lys | missense | 0 | 1 | 0 |
| M | sporadic ccRCC | 4 | 4 | mutated | 2 | c.354delCTTCinsT, p.Leu118_119del | in-frame | 0 | 1 | 0 |
| M | sporadic ccRCC | 3 | 3b | wild-type | / | / | LOH | 1 | 1 | 0 |
| F | sporadic ccRCC | 4 | 3b | mutated | 1 | c.214T > C, p.Ser72Pro | missense + LOH | 1 | 2 | 0 |
| F | sporadic ccRCC | 4 | 3b | mutated | 1 | c.340 + 2delT, fs site splice | splice + LOH | 1 | 2 | 0 |
| M | sporadic ccRCC | 3 | 2 | mutated | 1 | c.258insC, p.Pro86fs | frameshift + LOH | 1 | 2 | 1 |
| F | sporadic ccRCC | 3 | 3b | mutated | 1 | c.323ins20, p.Arg108fs | frameshift + LOH | 1 | 2 | 1 |
| F | sporadic ccRCC | 3 | 3b | mutated | 1 | c.287C > T, p.Gln96X | stop + LOH | 1 | 2 | 1 |
| F | sporadic ccRCC | 2 | 1b | mutated | 1 | c.223ins38, p.Ile75fS | frameshift + LOH | 1 | 2 | 1 |
| M | sporadic ccRCC | 2 | 1a | mutated | 1 | c.214del29, p.Ser78fs | frameshift + LOH | 1 | 2 | 1 |
| M | sporadic ccRCC | 2 | 3b | mutated | 3 | c.480delG, p.Glu160fs | frameshift + LOH | 1 | 2 | 1 |
| M | sporadic ccRCC | 2 | 3a | mutated | 3 | c.469del14, p.Thr157fs | frameshift + LOH | 1 | 2 | 1 |
| F | sporadic ccRCC | 2 | 1b | mutated | 1 | c.269delA, p.Asn90fs | frameshift + LOH | 1 | 2 | 1 |
| F | sporadic ccRCC | 2 | 3b | mutated | 3 | c.485delG, p.Cys162fs | frameshift + LOH | 1 | 2 | 1 |
| F | sporadic ccRCC | 1 | 1b | mutated | 1 | c.160del35, p.Met54fs | frameshift + LOH | 1 | 2 | 1 |

TABLE 3-continued

| Sex | Histology | Fuhrman's grade | Stage | VHL status | Mutated exon | Description of mutations | Type of alterations | Presence of LOH (C1) | Nb altered alleles (C2) | Presence LOF (C3) |
|---|---|---|---|---|---|---|---|---|---|---|
| F | sporadic ccRCC | 3 | 2 | wild-type | / | / | promoteur hypermethylation | 0 | 1 | 0 |
| M | sporadic ccRCC | 4 | 3b | wild-type | / | / | LOH | 1 | 1 | 0 |
| M | sporadic ccRCC | 3 | 2 | wild-type | / | / | promoteur hypermethylation | 0 | 1 | 0 |
| F | sporadic ccRCC | 2 | 3b | wild-type | / | / | promoteur hypermethylation + LOH | 1 | 2 | 1 |
| M | VHL-ccRCC | 2 | 1 | mutated | 3 | c.500G > A, p.Arg167Gln | missense | 0 | 1 | 0 |
| M | VHL-ccRCC | 3 | 2 | mutated | 1 | c.266T > A, p.Leu89His | missense | 0 | 1 | 0 |
| F | VHL-ccRCC | 2 | 1 | mutated | 1 | c.254T > C, p.Leu85Pro | missense | 0 | 1 | 0 |
| M | VHL-ccRCC | 2 | 2 | mutated | 1 | c.340 + 1G > T | splice + LOH | 1 | 2 | 0 |
| F | VHL-ccRCC | 2 | 3b | mutated | 2 | c.351G > T, p.Trp117Cys | missense + LOH | 1 | 2 | 0 |
| F | VHL-ccRCC | 2 | 1 | mutated | 1 | c.266T > C, p.Leu89His | missense + LOH | 1 | 2 | 0 |
| M | VHL-ccRCC | 2 | 2 | mutated | 1 | c.340 + 1G > T | splice + LOH | 1 | 2 | 0 |
| M | VHL-ccRCC | 3 | 3a | mutated | 1 | c.340 + 1G > T | splice + LOH | 1 | 2 | 0 |
| M | VHL-ccRCC | 1 | 1 | mutated | 2 | del ex2 + 3 | frameshift + LOH | 1 | 2 | 1 |
| M | VHL-ccRCC | 3 | 4 | mutated | 2 | del ex2 | frameshift + LOH | 1 | 2 | 1 |
| M | VHL-ccRCC | 2 | 1 | mutated | 1 | c.217C > T, p.Gln73X | stop + LOH | 1 | 2 | 1 |

The invention claimed is:

1. An in vitro or ex vivo method for selecting a patient affected with a tumor for a treatment with a PD-1/PD-L1 antibody or for determining whether a patient affected with a tumor is susceptible to benefit from a treatment with a PD-1/PD-L1 antibody, wherein said tumor is a clear cell renal cell carcinoma (ccRCC) and wherein the method comprises:
   (a) detecting if cells from a sample from said patient present with a loss of function of the von Hippel-Lindau (VHL) gene, wherein the loss of function of the VHL gene is predictive of the responsiveness of said patient to a treatment with a PD-1/PD-L1 antibody, and
   (b) selecting patients with loss of function of the VHL gene as suitable for a treatment with a PD-1/PD-L1 antibody, and
   (c) administering a PD-1/PD-L1 antibody to said patient with loss of function of the VHL gene.

2. The method according to claim 1, wherein the method further comprises a step of providing a sample from said patient.

3. The method according to claim 1, wherein the sample is a cancer sample.

4. The method according to claim 1, wherein the loss of function of the VHL gene is detected by:
   a) measuring the activity of the VHL protein;
   b) measuring the molecular weight of the VHL protein;
   c) measuring the expression level of the VHL gene;
   d) detecting the presence or the absence of mutations in VHL genes; or
   e) a combination of at least two of a)-d).

5. The method according to claim 4, wherein the loss of function of the VHL gene is determined by detecting the presence or the absence of mutations in VHL genes, the mutations being germline mutations, somatic mutations, nonsense mutations, missense mutations and/or promoter hypermethylation.

6. The method according to claim 1, wherein the PD-1/PD-L1 antibody targets PD-1, PD-L1 or the PD-1/PD-L1 complex.

7. The method according to claim 1, wherein the PD-1/PD-L1 antibody is selected from the group consisting of nivolumab, pembrolizumab, pidilizumab, AMP-224, AMP-514, BMS 936559, MPDL3280A (atezolizumab), durvalumab, avelumab and a combination thereof.

8. The method according to claim 1, wherein the patient is a mammal.

9. The method according to claim 8, wherein the patient has already received at least one line of treatment.

10. The method according to claim 8, wherein the mammal is a human.

* * * * *